United States Patent
Suda et al.

US011129900B2

(10) Patent No.: US 11,129,900 B2
(45) Date of Patent: Sep. 28, 2021

(54) CYTOPHILIC PEPTIDE-FUSED HIGH-DENSITY LIPOPROTEIN, AND DELIVERY OF DRUG TO POSTERIOR SEGMENT OF EYE BY OCULAR INSTALLATION OF SAID FUSION

(71) Applicants: KYOTO UNIVERSITY, Kyoto (JP); NOSTA AG, Basel (CH)

(72) Inventors: Kenji Suda, Kyoto (JP); Tatsuya Murakami, Toyama (JP); Nagahisa Yoshimura, Osaka (JP); Norimoto Gotoh, Fujinomiya (JP)

(73) Assignees: KYOTO UNIVERSITY, Kyoto (JP); NOSTA AG, Basel (CH)

( * ) Notice: Subject to any disclaimer, the term of this patent is extended or adjusted under 35 U.S.C. 154(b) by 0 days.

(21) Appl. No.: 15/539,276

(22) PCT Filed: Dec. 25, 2015

(86) PCT No.: PCT/JP2015/086203
§ 371 (c)(1),
(2) Date: Jun. 23, 2017

(87) PCT Pub. No.: WO2016/104690
PCT Pub. Date: Jun. 30, 2016

(65) Prior Publication Data
US 2018/0015171 A1 Jan. 18, 2018

(30) Foreign Application Priority Data
Dec. 25, 2014 (JP) .............................. JP2014-263018

(51) Int. Cl.
| | | |
|---|---|---|
| *A61K 47/64* | (2017.01) | |
| *A61K 47/69* | (2017.01) | |
| *C07K 14/775* | (2006.01) | |
| *A61P 21/02* | (2006.01) | |
| *A61K 45/00* | (2006.01) | |
| *A61K 47/42* | (2017.01) | |
| *C07K 19/00* | (2006.01) | |
| *C07K 7/06* | (2006.01) | |
| *C07K 7/08* | (2006.01) | |
| *A61P 9/10* | (2006.01) | |
| *A61P 27/02* | (2006.01) | |
| *A61P 27/06* | (2006.01) | |
| *A61P 27/12* | (2006.01) | |
| *A61P 27/10* | (2006.01) | |
| *A61K 9/00* | (2006.01) | |
| *A61K 47/24* | (2006.01) | |
| *A61K 31/506* | (2006.01) | |

(52) U.S. Cl.
CPC ............ *A61K 47/64* (2017.08); *A61K 9/0048* (2013.01); *A61K 45/00* (2013.01); *A61K 47/42* (2013.01); *A61K 47/6455* (2017.08); *A61K 47/6917* (2017.08); *A61P 9/10* (2018.01); *A61P 27/02* (2018.01); *A61P 27/06* (2018.01); *A61P 27/10* (2018.01); *A61P 27/12* (2018.01); *C07K 7/06* (2013.01); *C07K 7/08* (2013.01); *C07K 14/775* (2013.01); *C07K 19/00* (2013.01); *A61K 31/506* (2013.01); *A61K 47/24* (2013.01); *C07K 2319/01* (2013.01)

(58) Field of Classification Search
CPC .... C07K 14/775; C07K 19/00; A61K 47/645; A61K 47/6917
See application file for complete search history.

(56) References Cited

U.S. PATENT DOCUMENTS

| | | |
|---|---|---|
| 2011/0008421 A1 | 1/2011 | Hara et al. |
| 2013/0190226 A1* | 7/2013 | Wright ................ A61K 9/0019 514/1.9 |

FOREIGN PATENT DOCUMENTS

| | | |
|---|---|---|
| JP | 2010-280570 | 12/2010 |
| JP | 2011-246464 | 12/2011 |
| JP | 2013-525501 | 6/2013 |
| WO | 2009/107753 | 9/2009 |
| WO | 2011/069053 | 6/2011 |
| WO | 2011/140343 | 11/2011 |
| WO | 2012/012870 | 2/2012 |

OTHER PUBLICATIONS

Tripathi et al, Jan. 2013. Journal of General Virology, 94:40-49 (Year: 2013).*
Extended European Search Report dated May 28, 2018 in corresponding European patent application No. 15873258.6.
Marta Marchesi et al., "Apolipoprotein A-I$_{Milano}$/POPC complex attenuates post-ischemic ventricular dysfunction in the isolated rabbit heart", Atherosclerosis, 2007, vol. 197, No. 2, pp. 572-578.
International Search Report dated Mar. 15, 2016 in International (PCT) Application No. PCT/JP2015/086203.

(Continued)

*Primary Examiner* — Zachary C Howard
(74) *Attorney, Agent, or Firm* — Wenderoth, Lind & Ponack, L.L.P.

(57) ABSTRACT

The purpose of the present invention is to provide a novel system for the delivery of a drug to a posterior segment of the eye. The present invention relates to: a cytophilic peptide-fused high-density lipoprotein (cHDL) which can be used as a carrier for the delivery of a drug to a posterior segment of the eye; a method for producing the cytophilic peptide-fused high-density lipoprotein; a system of the delivery of a drug to a posterior segment of the eye, a pharmaceutical composition, and a system of the delivery of a drug to a posterior segment of the eye, each of which utilizes the cytophilic peptide-fused high-density lipoprotein; and a method for diagnosing, preventing or treating posterior ocular disease.

18 Claims, 13 Drawing Sheets

(56) References Cited

OTHER PUBLICATIONS

English translation of the International Preliminary Report on Patentability dated Dec. 28, 2016 in International (PCT) Application No. PCT/JP2015/086203.

Hironaka et al., "Design and evaluation of a liposomal delivery system targeting the posterior segment of the eye", Journal of Controlled Release, 136:247-253 (2009).

Kompella et al., "Luteinizing hormone-releasing hormone agonist and transferrin functionalizations enhance nanoparticle delivery in a novel bovine ex vivo eye model", Molecular Vision, 12:1185-1198 (2006).

Murakami et al., "Intracellular drug delivery by genetically engineered high-density lipoprotein nanoparticles", Nanomedicine (London, UK), 5(6):867-879 (2010).

Kompella et al., "Nanomedicines for back of the eye drug delivery, gene delivery, and imaging", Progress in Retinal and Eye Research, 36:172-198 (2013).

Gotto, Jr. et al., "Introduction to Plasma Lipoproteins", Methods in Enzymology, 128:3-41 (1986).

Yafai et al., "Anti-angiogenic effects of the receptor tyrosine kinase inhibitor, pazopanib, on choroidal neovascularization in rats", European Journal of Pharmacology, 666:12-18 (2011).

Escudero-Ortiz et al., "Development and Validation of an HPLC-UV Method for Pazopanib Quantification in Human Plasma and Application to Patients With Cancer in Routine Clinical Practice", Ther Drug Monit., 37(2):172-179 (2015).

Murakami et al., "1-C-11 Preparation of Cell invaded Lipoprotein Nanoparticles using Genetic Engineering Method", Drug Delivery System, 24(3):301 (2009), with English Translation.

Mathew et al., "Exclusive Photothermal Heat Generation by a Gadolinium Bis(naphthalocyanine) Complex and Inclusion into Modified High-Density Lipoprotein Nanocarriers for Therapeutic Applications", ACS NANO, 7(10):8908-8916 (2013).

Kim et al., "Development of Cationic Peptide-Fused High-Density Lipoprotein", Proceedings of The Japan Biomaterials Congress, 35:338 (2013), with English translation.

Murakami et al., "Size control of lipid-based drug carrier by drug loading", Molecular BioSystems, 6:789-791 (2010).

Murakami et al., "3OD3-5 High-functionality of lipoprotein which aims a DDS Application", Drug Delivery System, 23(3):383 (2008), with English translation.

Tahara et al., "Development of Biocompatible Nanoparticle Eyedrop Preparations which aims Drug Delivery to Posterior Segment", Daiwa Securities Health Foundation, 36:73-76 (2013), with Partial English translation.

Hironaka et al., "Design of liposome eyedrop preparations which aims drug Delivery to the Posterior segment", Abstract of Annual Meeting of the Pharmaceutical Society of Japan, 128(4):112 (2008), with English translation.

Karasawa et al., "Study on poly-L-Arginine—modified liposome which aims delivery to the posterior segment", Proceedings of The Annual Meeting of the Japan Society of Drug Delivery System (DDS), 28:172 (2012), with English translation.

Kaur et al., "Nanotherapy for posterior eye diseases", Journal of Controlled Release, 193:100-112 (2014).

Wang et al., "Apolipoprotein A—I Binds and Inhibits Human Antibacterial/Cytotoxic Peptide LL-37", The Journal of Biological Chemistry, 273(50):33115-33118 (1998).

Wang et al., "The antimicrobial peptide LL-37 binds to the human plasma protein apolipoprotein A—I", Rapid Communications in Mass Spectrometry, 18(5):588-589.

Notice of Reasons for Refusal dated Oct. 29, 2019 in corresponding Japanese Patent Application No. 2016-566501, with English Translation.

Kajiwara et al., "Cell-penetrating Peptide", Journal of Pharmaceutical Affairs, 2013, vol. 141, pp. 220-221.

Shiroh Futaki, "Intracellular delivery of biopolymers using membrane-permeable peptides", Membrane, 2003, vol. 28, No. 2, pp. 55-60.

* cited by examiner

Progress in Retinal and Eye Research 2013;36:172-198

DMPC

DPPC

DSPC

Inner layer
of the retina

Outer layer
of the retina

Choroid
membrane

CPP absent

TAT

Inner layer
of the retina

Outer layer
of the retina

Choroid
membrane

PEN

R8

*P* = 0.028

*P* = 0.034

CYTOPHILIC PEPTIDE-FUSED HIGH-DENSITY LIPOPROTEIN, AND DELIVERY OF DRUG TO POSTERIOR SEGMENT OF EYE BY OCULAR INSTALLATION OF SAID FUSION

TECHNICAL FIELD

The present invention relates to drug delivery of a high-density lipoprotein (HDL) or a complex of the same and a cytophilic peptide to the posterior eye segment by ocular instillation. More specifically, the present invention relates to a cytophilic peptide-bound high-density lipoprotein used as a carrier for delivering a drug to the posterior eye segment, a pharmaceutical composition comprising the high-density lipoprotein which is enclosed by a drug for treating a disease of the posterior eye segment, and a system for delivery a drug to the posterior eye segment by using the high-density lipoprotein.

BACKGROUND ART

Recently, for treating diseases of the posterior eye segment such as age-related macular degeneration and diabetic retinopathy, intravitreal injection of a drug has come to be used. In such an invasive local administration method, since a drug is directly injected into the eye, a reliable treatment effect can be expected; however, injection has drawbacks in that there is a risk of developing endophthalmitis and cumbersome repetitive injection is required. Unfortunately, in the eye, there is a barrier function for regulating transfer of a substance from the outside into the eye. Due to the barrier, it is not easy to deliver a drug into the eyeball by noninvasive administration such as ocular instillation and intravenous administration, in particular, the efficiency of a drug in delivering to the posterior eye segment such as retina is extremely low. The various routes for intraocular drug delivery are shown in FIG. 1.

To solve this problem, development of drug delivery using a carrier, i.e., a drug carrier by ocular instillation, has been attempted. Of the carriers, a bio nano-material has advantages: since the nano-material is constituted of a biological material, a biological defense reaction to the carrier is expected to rarely occur; and a medicinal effect is expected to last longer owing to the dynamic characteristics of a nano-material. In the present invention, a high-density lipoprotein (HDL), which is a bio-nano material mainly responsible for lipid transport in blood, is focused on. The diameter of a HDL particle is as small as about less than 100 nano-meter (nm) and, in addition, various functions such as cytophilic property and cumulative property on vascular endothelial cells, can be provided to the HDL by a protein-engineering approach. Based on these, HDL is expected to be suitable as a drug delivery carrier to the posterior eye segment by ocular instillation.

As the drug carrier currently used in the ophthalmological field, a liposome for use in delivery to the posterior eye segment has been known (Patent Literatures 1 and 2). In the liposome for use in delivery to the posterior eye segment, it has been known that a fluorescent dye, i.e., coumarin-6, is allowed to enclose in the liposome and the fluorescence intensity thereof is measured to check drug delivery to the posterior eye segment.

In connection with the liposome for use in delivery to the posterior eye segment, another report teaches that as the size of the liposome decreases, reachability of the liposome to the posterior eye segment increases, with the result that it is expected to increase accumulation of a drug (Non Patent Literature 1). In another report, it is also suggested that the size of a drug carrier for ocular instillation is desirably 20 nm or less (Non Patent Literature 2).

Unfortunately, there are not many literatures reporting that a liposome of less than 100 nm in size can be produced. Accordingly, in order to improve the efficiency of drug delivery, it has been desired to produce a novel biomaterial, which is likely to produce the nano-material further reduced in size.

The high-density lipoprotein (cHDL) having a cytophilic peptide fused thereto so far known is designed for delivering an anticancer agent into malignant tumor cells (Non Patent Literature 3); whereas, lipoproteins including HDL, having a particle size of 100 nm or less and designed for delivering a drug in the form of an eye-drop, have not yet been known.

If a functional peptide such as a cytophilic peptide is fused into a high-density lipoprotein (HDL), the fused high-density lipoprotein itself can acquire a novel dynamic characteristic and the bioactivity intrinsic to the fused functional peptide itself can be imparted to the high-density lipoprotein (HDL) that the peptide is contained.

CITATION LIST

Patent Literatures

Patent Literature 1: International Publication No. WO 2009/107753
Patent Literature 2: Japanese Patent Laid-Open No. 2011-246464

Non Patent Literatures

Non Patent Literature 1: Kohei Hironaka et al., J Controlled Release 2009; 136: 247-53,
Non Patent Literature 2: Kompella, U. B. et al., Molecular Vision 2006; 12: 1185-1198
Non Patent Literature 3: Tatsuya Murakami et al., Nanomedicine (London, U. K.) 2010; 5: 867-79

SUMMARY OF INVENTION

Technical Problem

The present inventors conducted intensive studies on high-density lipoproteins (HDL). As a result, they found that HDL (for example, reconstructed (i.e., artificial) HDL (rHDL)) can deliver a compound (for example, a drug) enclosed therein to the posterior eye segment, and that HDL to which a functional peptide, in particular, a cytophilic peptide (CP) is bound (for example, fused), i.e., high-density lipoprotein (cHDL) binding to the cytophilic peptide (CP), can further increase the delivery amount, with the result that HDL becomes useful as a carrier for delivering a drug to the posterior eye segment by ocular instillation. Thus, the present invention provides a high-density lipoprotein (cHDL) to which a cytotoxicity-free and cytophilic peptide is bound (for example, fused), capable of delivering a compound (for example, a drug) enclosed therein to the posterior eye segment, and provides a method for preparing cHDL. The present invention also provides a drug delivery system using the cytophilic peptide-bound high-density lipoprotein to the posterior eye segment; a pharmaceutical composition comprising the high-density lipoprotein and a drug for diagnosis, prevention or treatment of a disease of the posterior eye segment; and a method for diagnosis, prevention or treatment of a disease of the posterior eye segment by using the drug delivery system or the pharmaceutical composition.

Solution to Problem

The present invention provides the following embodiments but is not limited to them.

[1] A high-density lipoprotein as a carrier for delivering a drug to the posterior eye segment.

[2] A cytophilic peptide-bound high-density lipoprotein as a carrier for delivering a drug to the posterior eye segment, comprising a high-density lipoprotein and a cytophilic peptide.

[3] The high-density lipoprotein according to [1] or the cytophilic peptide-bound high-density lipoprotein according to [2], in which the high-density lipoprotein contains an apolipoprotein and a phospholipid.

[4] The cytophilic peptide-bound high-density lipoprotein according to [2] or [3], in which the cytophilic peptide is a cell membrane permeable peptide.

[4-1] The cytophilic peptide-bound high-density lipoprotein according to [2] or [3], in which the cytophilic peptide is a basic cell membrane permeable peptide.

[5] The cytophilic peptide-bound high-density lipoprotein according to any one of [2] to [4], in which the cytophilic peptide is a bound protein bound onto the apolipoprotein.

[6] The high-density lipoprotein according to [1] or the cytophilic peptide-bound high-density lipoprotein according to any one of [2] to [5], in which the apolipoprotein is at least one kind selected from the group consisting of apolipoprotein A-I, apolipoprotein A-II, apolipoprotein C, apolipoprotein E, a partial fragment thereof, and a genetically modified apolipoprotein thereof.

[6-1] The high-density lipoprotein according to [1] or the cytophilic peptide-bound high-density lipoprotein according to any one of [2] to [5], in which the apolipoprotein is at least one kind selected from the group consisting of apolipoprotein A-I and a genetically modified apolipoprotein A-I thereof.

[7] The cytophilic peptide-bound high-density lipoprotein according to any one of [2] to [6], in which the cytophilic peptide is at least one kind selected from the group consisting of TAT peptide, penetratin, polyarginine (R8), polyhistidine (H16), LL-37, transportan, Pep-1 and MTS.

[8] The high-density lipoprotein according to [1] or the cytophilic peptide-bound high-density lipoprotein according to any one of [2] to [7], in which the phospholipid is phosphatidylcholine.

[8-1] The high-density lipoprotein according to [1] or the cytophilic peptide-bound high-density lipoprotein according to any one of [2] to [7], in which the phospholipid is a glycerophospholipid of a fatty acid group having 12 to 18 carbon atoms.

[9] The high-density lipoprotein according to [1] or the cytophilic peptide-bound high-density lipoprotein according to any one of [2] to [8], having a particle size of less than 100 nm in diameter.

[9-1] The high-density lipoprotein according to [1] or the cytophilic peptide-bound high-density lipoprotein according to any one of [2] to [8], having a particle size ranging from 10 to 20 nm in diameter.

[10] A complex comprising the high-density lipoprotein according to [1] or the cytophilic peptide-bound high-density lipoprotein according to any one of [2] to [9], further comprising at least one molecule of at least one compound selected from a fluorescent labeling substance, a bioactive substance or a drug, per molecule of the high-density lipoprotein according to [1].

[11] The high-density lipoprotein according to [1], the cytophilic peptide-bound high-density lipoprotein according to any one of [2] to [9], or the complex according to [10], each for ocular instillation.

[12] A system for delivering a drug to the posterior eye segment, comprising the high-density lipoprotein according to [1] or the cytophilic peptide-bound high-density lipoprotein according to any one of [2] to [9], and a drug effective for diagnosis, prevention or treatment of a disease of the posterior eye segment.

[13] A pharmaceutical composition for diagnosis, prevention or treatment of a disease of the posterior eye segment, comprising the high-density lipoprotein according to [1] or the cytophilic peptide-bound high-density lipoprotein according to any one of [2] to [9], a drug effective for diagnosis, prevention or treatment of a disease of the posterior eye segment which is contained in the high-density lipoprotein, and a pharmaceutically acceptable additive.

[14] A method for diagnosis or treatment of a disease of the posterior eye segment, which comprises using the system for delivering a drug to the posterior eye segment according to [12] or the pharmaceutical composition according to [13].

[15] The system for delivering a drug to the posterior eye segment according to [12], the pharmaceutical composition for diagnosis, prevention or treatment of a disease of the posterior eye segment according to [13] or the method for diagnosis, prevention or treatment of a posterior eye disease according to [14], in which the disease of the posterior eye segment is at least one disease selected from the group consisting of age-related macular degeneration, diabetic retinopathy, diabetic macular edema, glaucoma, retinal artery or vein obstruction, retinal degenerative disease, degenerative myopia, macular hole, macular epithelium, retinal detachment, cataract, vitreous opacity and uveitis.

[15-1] The system for delivering a drug to the posterior eye segment according to [12], the pharmaceutical composition for diagnosis, prevention or treatment of a disease of the posterior eye segment according to [13], or the method for diagnosis, prevention or treatment of a posterior eye segment according to [14], in which the disease of the posterior eye segment is at least one disease selected from the group consisting of age-related macular degeneration, diabetic retinopathy, diabetic macular edema and retinal artery or vein obstruction.

[15-2] The system for delivering a drug to the posterior eye segment according to [12], the pharmaceutical composition for diagnosis, prevention or treatment of a disease of the posterior eye segment according to [13], or the method for diagnosis, prevention or treatment of a posterior eye segment according to [14], each for ocular instillation.

[16] A method for producing the cytophilic peptide-bound high-density lipoprotein according to any one of [2] to [9] or the complex according to [10], comprising i) binding a cytophilic peptide to an apolipoprotein to obtain a bound protein;

ii) a) blending a liposome containing a phospholipid, at least one compound selected from a fluorescent labeling substance, a bioactive substance or a drug, with the bound protein obtained in the above i) to produce a crude high-density lipoprotein having the cytophilic peptide bound thereto; or, b) mixing an available cholate micelle with at least one compound selected from a bioactive substance or a drug to produce a crude high-density lipoprotein having the cytophilic peptide bound thereto; and iii) removing unreacted liposome, phospholipid micelle and/or apolipoprotein by an ultracentrifugation method to purify the crude high-density lipoprotein having the cytophilic peptide bound thereto.

[17] Use of the high-density lipoprotein according to [1] or the cytophilic peptide-bound high-density lipoprotein according to any one of [2] to [9], the pharmaceutical composition according to [13] in the manufacture of a medicament for diagnosis, prevention or treatment of a disease of the posterior eye segment.

[18] The high-density lipoprotein according to [1] or the cytophilic peptide-bound high-density lipoprotein according to any one of [2] to [9], or the pharmaceutical composition according to [13], each for use in diagnosis, prevention or treatment of a disease of the posterior eye segment.

[19] A cytophilic peptide-bound high-density lipoprotein (cHDL), which comprises
  a) a high-density lipoprotein (HDL) containing an apolipoprotein and a phospholipid,
  wherein the apolipoprotein is at least one kind of apolipoprotein selected from the group consisting of apolipoprotein A-I and a genetically modified apolipoprotein A-I thereof, and
  the phospholipid is a glycerophospholipid of a fatty acid group having 12 to 18 carbon atoms;
  b) a cytophilic peptide (CPP) selected from the group consisting of basic cell membrane permeable peptides; and
  c) optionally, at least one compound selected from a fluorescent labeling substance, a bioactive substance or a drug, and
which has a particle size of less than 100 nm in diameter (for example, 10 to 20 nm in diameter).

[20] A pharmaceutical composition for diagnosis, prevention or treatment of at least one disease selected from the group consisting of
age-related macular degeneration, diabetic retinopathy, diabetic macular edema and retinal artery or vein obstruction, comprising
1) a cytophilic peptide-bound high-density lipoprotein, which comprises
  a) high-density lipoprotein (HDL) containing an apolipoprotein and a phospholipid, wherein
  the apolipoprotein is at least one kind of apolipoprotein selected from the group consisting of apolipoprotein A-I and a genetically modified apolipoprotein A-I thereof, and
  the phospholipid is a glycerophospholipid of a fatty acid group having 12 to 18 carbon atoms;
  b) a cytophilic peptide selected from the group consisting of basic cell membrane permeable peptides; and
  c) at least one compound appropriately selected from a compound which serves as a drug for suppressing intraocular neovascularization (for example, choroidal neovascularization), or a diagnostic, prophylactic or therapeutic agent for a disease selected from the group consisting of age-related macular degeneration, diabetic retinopathy, diabetic macular edema and retinal artery or vein obstruction, and,
  which has a particle size of less than 100 nm in diameter (for example, 10 to 20 nm in diameter), and 2) a pharmaceutically acceptable additive.

Effects of Invention

The high-density lipoprotein (cHDL) comprising the cytophilic peptide of the present invention can deliver a compound (drug) enclosed therein to the posterior eye segment, with the result that the compound is highly accumulated in the retinal cell tissue. Furthermore, the cHDL of the present invention has no cytotoxicity. Thus, a high-density lipoprotein to which the cytophilic peptide of the present invention is bound (for example, fused) is useful as a carrier for delivering a drug to the posterior eye segment by ocular instillation. Owing to this, if a drug for diagnosis, prevention or treatment of a disease of the posterior eye segment is enclosed in the cHDL of the present invention, the drug can be delivered in high concentration to the posterior eye segment, which can provide improving treatment effect and reducing side effects of the drug. For example, a remarkable effect can be attained for suppressing neovascularization. Moreover, since noninvasive local administration by ocular instillation can be made, a risk of side effects such as endophthalmitis caused by invasive local administration can be reduced and/or cumbersome repetitive injection can be avoided.

In the figure, the comparison results on cHDL in the case where DMPC, DPPC or DSPC was used, 30 minutes after ocular instillation are shown.

Figure 9:
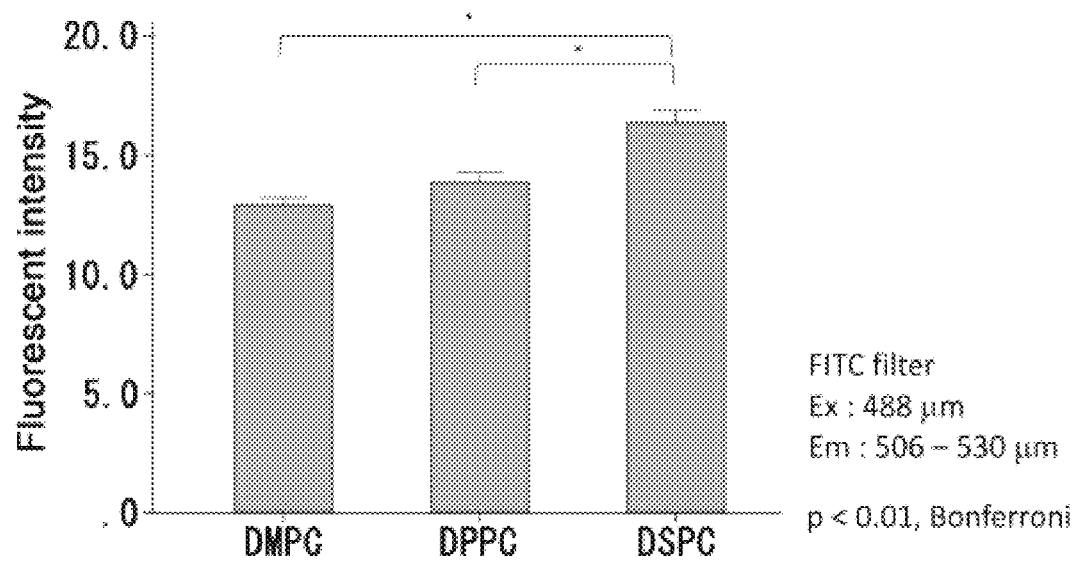
Figure 10:
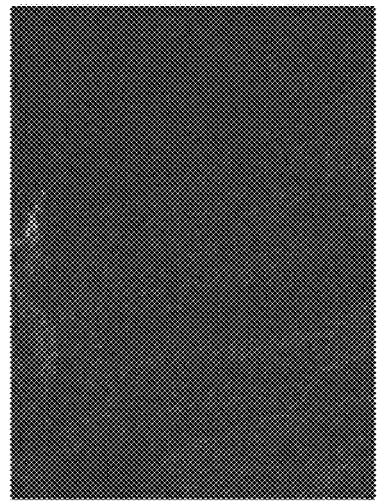
Figure 10:
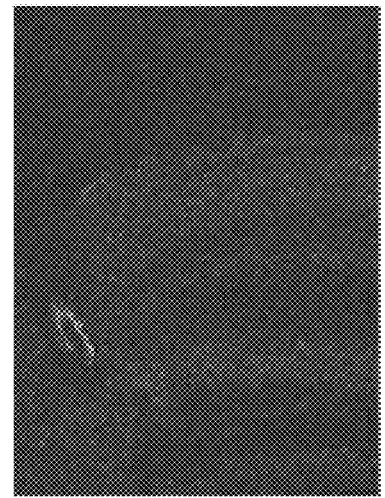
Figure 10:
Figure 10:
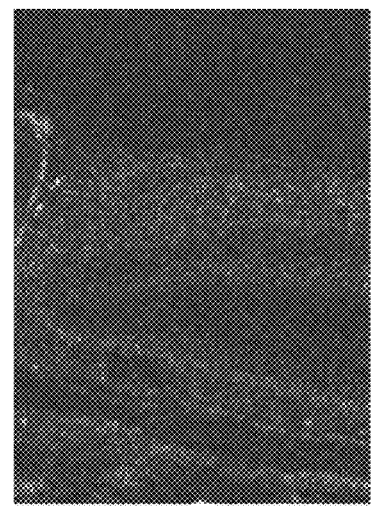

FIG. 9 is a graph showing digitalized fluorescence intensity resulting from a delivery confirmation test to the posterior eye segment cell tissue and obtained in FIG. 10. In the graph, the comparison results of cHDLs using DMPC, DPPC or DSPC are shown.

FIG. 10 shows observation results by a fluorescent microscopy, showing the results of a delivery confirmation test to the posterior eye segment cell tissue, in which the cases of cHDL using TAT peptide, penetratin (PEN) peptide and polyarginine (R8) are used as a cytophilic peptide (CPP) are compared to the case of CPP-free cHDL. The images show the results of the cHDLs in the cases of TAT peptide, penetratin (PEN) peptide and polyarginine (R8) in comparison with the case of CPP-free cHDL 30 minutes after ocular instillation.

Figure 11:
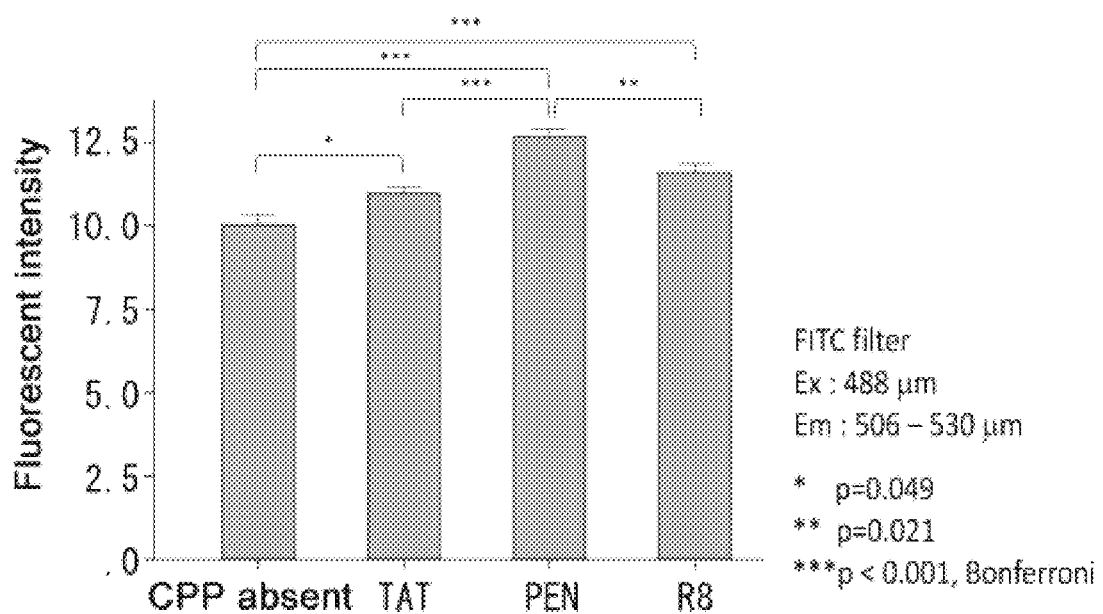

FIG. 11 is a graph showing digitalized fluorescence intensity resulting from a delivery confirmation test to the posterior eye segment cell tissue and obtained in FIG. 10. In the graph, the results of each of the cHDL in the presence of TAT peptide, penetratin (PEN) peptide or polyarginine (R8) are shown in comparison with the case of the cHDL in absence of CPP.

Figure 12:
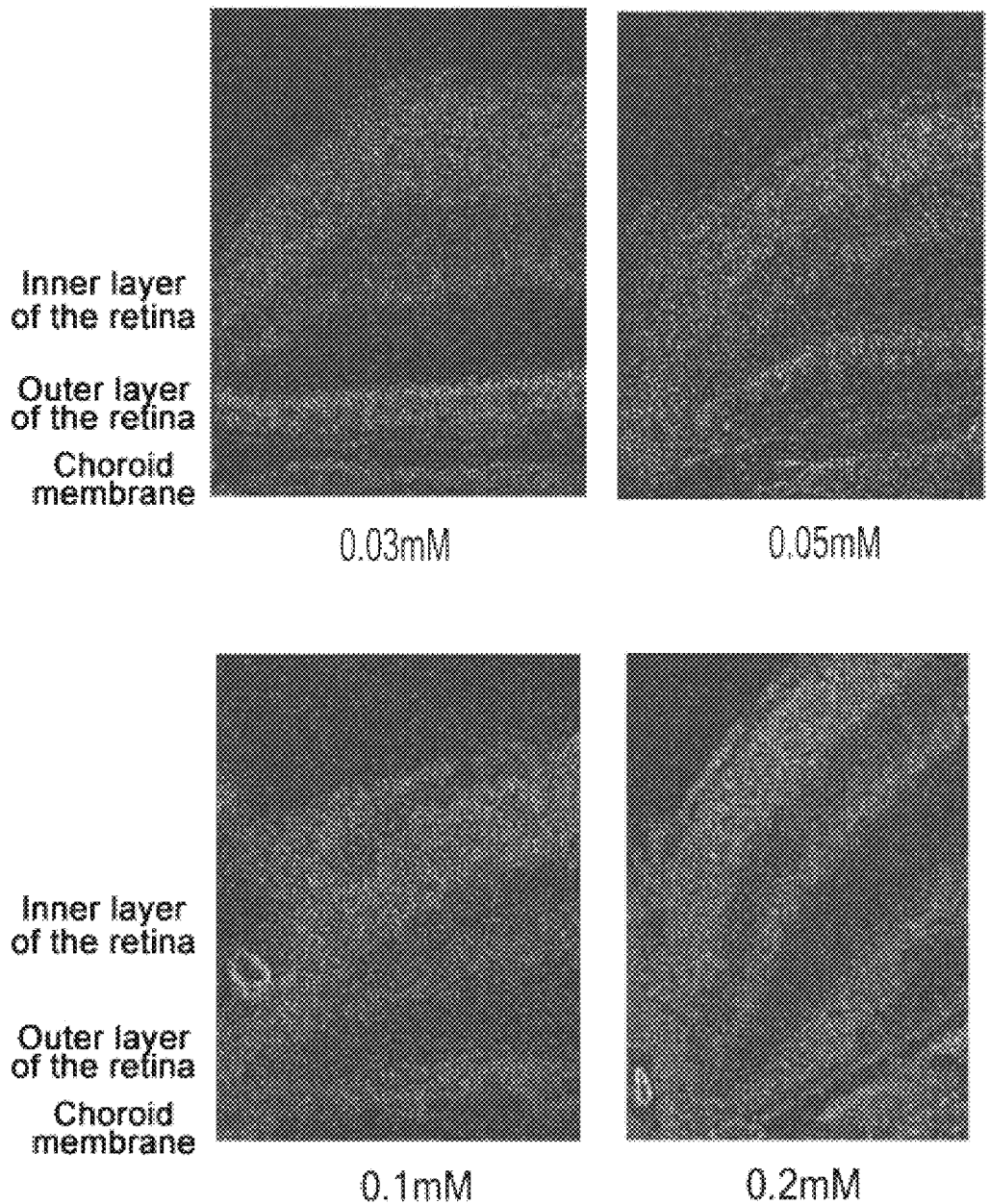

FIG. 12 shows the observation results by a fluorescent microscopy, showing the results of a delivery confirmation test to the posterior eye segment cell tissue, on cHDLs produced by using coumarin-6 in different concentrations. The figures show the comparison results of cHDLs containing coumarin-6 in concentrations of 0.03 mM, 0.05 mM, 0.1 mM or 0.2 mM, 30 minutes after ocular instillation.

Figure 13:
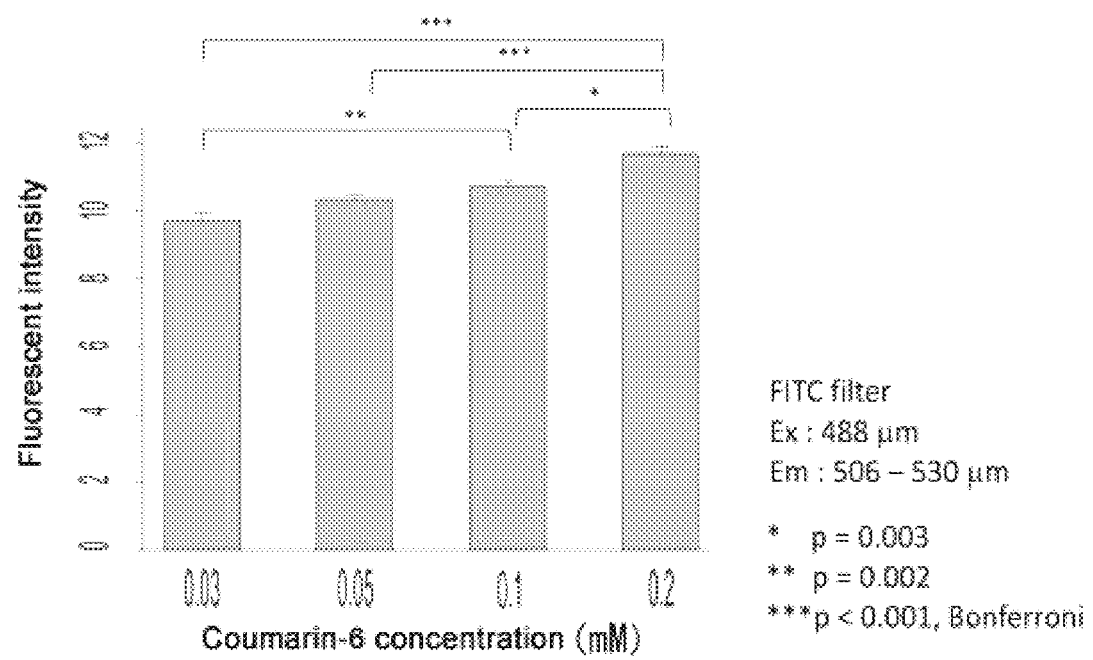

FIG. 13 is a graph showing digitalized fluorescence intensity resulting from a delivery confirmation test to the posterior eye segment cell tissue and obtained in FIG. 12. In the graph, the comparison results of cHDLs containing coumarin-6 in concentrations of 0.03 mM, 0.05 mM, 0.1 mM or 0.2 mM are shown.

Figure 14:
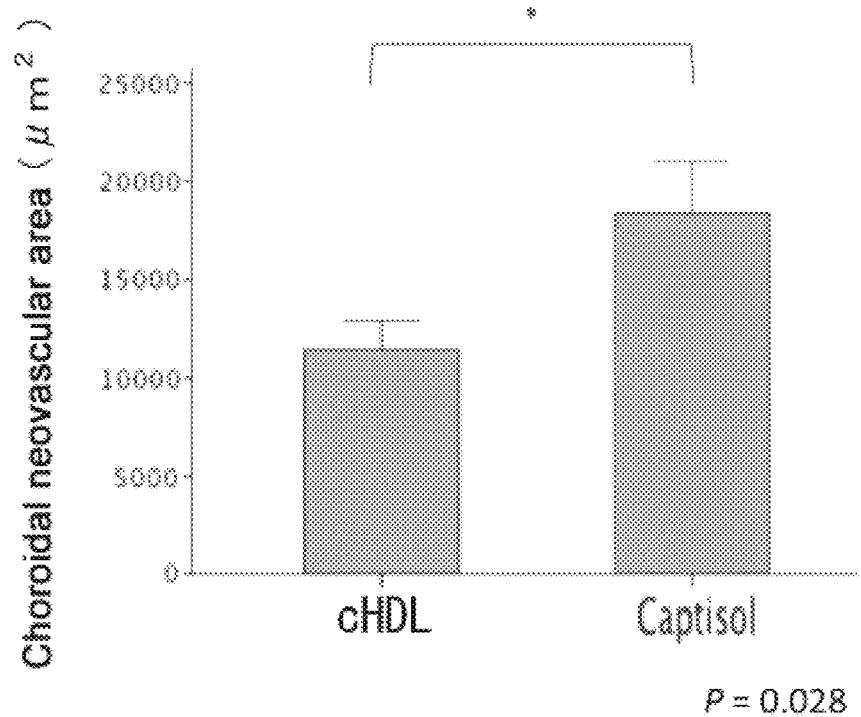
Figure 14:
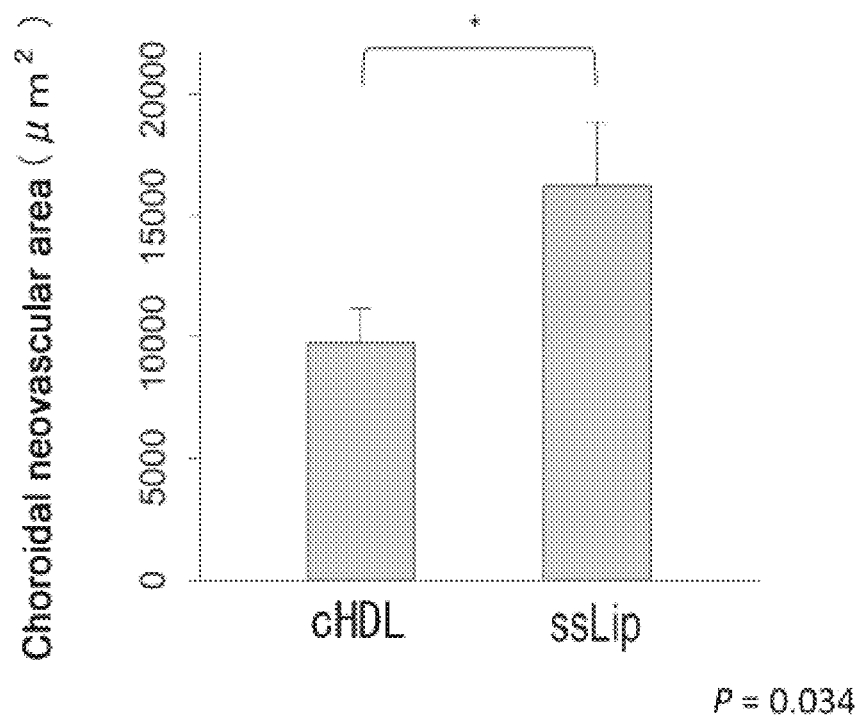

FIG. 14 is a graph showing the results of suppression of a choroidal neovascular area after ocular instillation in a neovascularization model test by a system for delivering a drug to the posterior eye segment, when Pazopanib is used as a drug, in which the case of a complex where cHDL is used as a carrier is compared to the case of a complex where captisole or ssLip described in Example 3 is used as a positive control. In the graph, the results show the case of cHDL in comparison with the case of captisole; and the case of cHDL in comparison with the case of ssLip.

DESCRIPTION OF EMBODIMENTS

Now, the present invention will be more specifically described below.
(Definition)
The terms to be used in the specification and claims will be defined below.

The high-density lipoprotein (HDL) as used herein refers to a lipoprotein containing apolipoprotein A-I (apoA-I), and may be any one of a high-density lipoprotein derived from plasma naturally obtained, or a reconstructed (more specifically, artificial) high-density lipoprotein (rHDL) which is produced from an apolipoprotein or a genetically modified apolipoprotein and a phospholipid by a chemical synthetic approach or a genetic engineering approach. The high-density lipoprotein (HDL) contains an apolipoprotein and a phospholipid as major components. When a high-density lipoprotein (HDL) is artificially prepared, a phospholipid can be used in an amount several tens to several hundred times as large as one mole of an apolipoprotein. If a functional peptide, i.e., a cytophilic peptide (CP) is appropriately bound (for example, fused) to the high-density lipoprotein (HDL), a cytophilic peptide-bound (for example, fused) high-density lipoprotein (cHDL) can be obtained. In addition, a fluorescent labeling substance may be contained as an optional component. The high-density lipoprotein (HDL) or the cytophilic peptide-bound high-density lipoprotein (cHDL) can be used as a carrier for delivering a drug to the posterior eye segment.

The density of HDL used herein, in the case of a naturally occurring HDL, falls within the range of about 1.063 to 1.210 g/mL (see, Antonio M. Gotto, Jr. et al., Methods Enzymol. 1986; 128: 3-41); whereas, in the case of rHDL, the density is specified in accordance with the density of a naturally occurring HDL; however, the density can be controlled to be a desired value during production. Because of this, for example, the density of a natural low-density lipoprotein (LDL) being within the range of about 1.019 to about 1.063 g/mL (see, the above literature of Antonio M. Gotto, Jr. et al.) can be also included.

The particle size of the high-density lipoprotein (HDL) in the case of a naturally occurring HDL falls within the range of about 5 to 12 nm (see, the above literature of Antonio M. Gotto, Jr. et al.); whereas in the case of rHDL, the particle size is specified in accordance with the particle size of a naturally occurring HDL; however, the particle size can be controlled to be a desired value during production. Because of this, for example, a diameter being within the range of about 18 to about 25 nm, which is a particle size of a natural LDL, can be also included (see, the above literature of Antonio M. Gotto, Jr. et al.). The particle size (diameter) can be also controlled to be less than about 1000 nm, less than about 200 nm, or less than about 100 nm. The high-density lipoprotein of the present invention as used herein is expected to be increased in reachability to the posterior eye segment as the size thereof decreases, regardless of the presence or absence of binding (for example, fusion) of a cytophilic peptide. Accordingly, the particle size (diameter) thereof may be typically less than about 100 nm, preferably about 10 to about 50 nm and more preferably about 10 to about 20 nm.

A component, "apolipoprotein", refers to a protein moiety constituting a lipoprotein, except for the lipid. Examples of the apolipoprotein in the present invention include, but are not limited to, an apolipoprotein generally known to be contained in a natural lipoprotein and a genetically modified apolipoprotein thereof. The apolipoprotein known to be contained in a high-density lipoprotein (HDL) and a genetically modified apolipoprotein thereof are preferable. For example, proteins belonging to groups of apolipoproteins A to E are included, and preferably, at least one kind selected from the group consisting of apolipoprotein A-I (apoA-I), apolipoprotein A-II (apoA-II), apolipoprotein C (apoC), apolipoprotein E (apoE) and a genetically modified apolipoprotein thereof are included, however, the apolipoprotein is not limited to them. More preferably, apolipoprotein A-I (apoA-I) and a genetically modified apoA-I thereof can be included. The genetically modified apolipoprotein refers to e.g., a mutant or analog having the same function as the function (for example, lipid binding function) of an apolipoprotein (in other words, a functionally equivalent substance). For example, a partial fragment of an apolipoprotein and an apolipoprotein composed of the partial fragments in combination are included. Examples of the genetically modified apolipoprotein obtained from apolipoprotein A-I include N-terminal 43 amino acid deficient apoA-I.

A component, "phospholipid" used herein, refers to a lipid having a single or a plurality of phosphoric acid esters. In the present invention, the phospholipid includes a phospholipid, which generally known to be contained in a natural lipoprotein. A phospholipid known to be contained in a high-density lipoprotein (HDL) is preferable; however, the phospholipid is not limited to them. For example, a glycerophospholipid having a glycerin skeleton and a sphingophospholipid having a sphingosine as a skeleton are included. Examples of the sphingophospholipid include sphingomyelin, sphingosine-1-phosphoric acid and ceramide.

Examples of the glycerophospholipid include phosphatidylglycerol, phosphatidylserine, phosphatidylcholine and phosphatidylethanolamine, and phosphatidylcholine are preferable. A long-chain glycerophospholipid, which has an alkyl group (present in an acyl group) having about 9 to about 23 carbon atoms (i.e., a fatty acid group having about 10 to 24 carbon atoms), preferably about 11 to about 17 carbon atoms (i.e., a fatty acid group having about 12 to 18 carbon atoms) and more preferably about 13 to about 17 carbon atoms (i.e., a fatty acid group having about 14 to 18 carbon atoms), are preferable. The fatty acid group used herein may contain one or more carbon-carbon unsaturated double bonds; however, a carbon-carbon unsaturated double bond is preferably not contained. Typical examples of glycerophospholipid include, but are not limited to, dilauroylphosphatidylcholine (DLPC), dimyristoylphosphatidylcholine (DMPC), dipalmitoylphosphatidylcholine (DPPC), distearoylphosphatidylcholine (DSPC), egg phosphatidylcholine (PC) and 1-palmitoyl-2-oleoylphosphatidylcholine (POPC). The phospholipids can be used alone or in combination of two or more. In the present invention, it is presumed that the phospholipid controls, for example, the hardness of lipid membrane, and plays a role in contributing to form a stabilized complex and further enclose a compound such as a drug.

A component, "cytophilic peptide (CP)" used herein, refers to a peptide having cell affinity enough to bind to cell membrane and thereafter migrate into the cell. Examples of the cell affinity used herein include, but are not limited to, cell membrane permeability, cell adhesiveness, vascular endothelial cell accumulation, endosomal escape activity, cell nuclear accumulation, and mitochondrial accumulation.

In the present invention, examples of the cytophilic peptide include a natural peptide derived from a natural protein and a synthetic peptide (for example, a chimeric peptide) artificially produced. Examples of the cytophilic peptide include a basic cytophilic peptide, an amphiphilic cytophilic peptide and a hydrophobic cytophilic peptide, which are classified depending upon the chemical property based on the amino acid sequence. A basic cytophilic peptide is preferable and a basic cell membrane permeable peptide is more preferable. For example, at least one kind selected from the group consisting of basic cytophilic peptides (for example, HIV-1 virus TAT protein (Trans-activator of transcription protein)-derived TAT peptide, drosophila-derived penetratin (PEN), polyarginine (for example, arginine octamer (R8)), polyhistidine ((for example, histidine hexadecamer (H16)), antimicrobial peptide-derived LL-37 peptide); amphiphilic cytophilic peptides (for example, chimeric peptide, transportan and Pep-1 peptide); and hydrophobic cytophilic peptides (for example, a synthetic peptide, Pep-1 peptide, obtained by a phage display method, a signal peptide (membrane protein)-derived peptide, i.e., mitochondrial targeting signal (MTS)); however, the cytophilic peptide is not limited to them.

Figure 1:
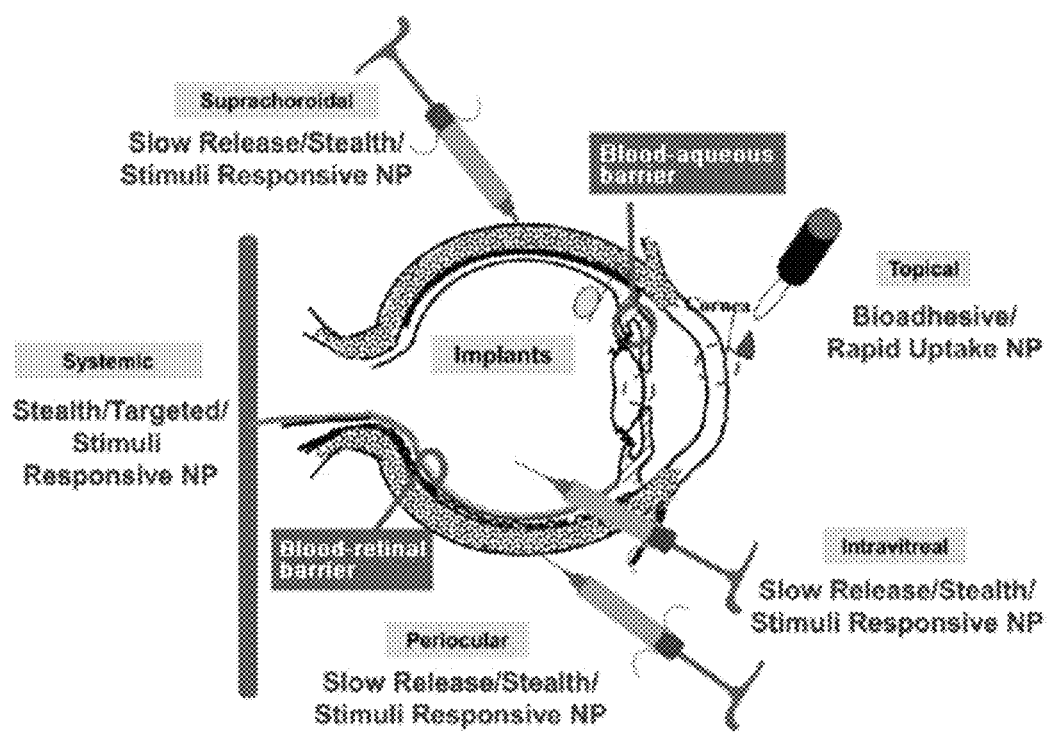
FIG. 1 is an illustration schematically showing various administration routes for intraocular drug delivery. The schematic illustration is described in Progress in Retinal and Eye Research 2013, 36: 172-198.
Figure 2:
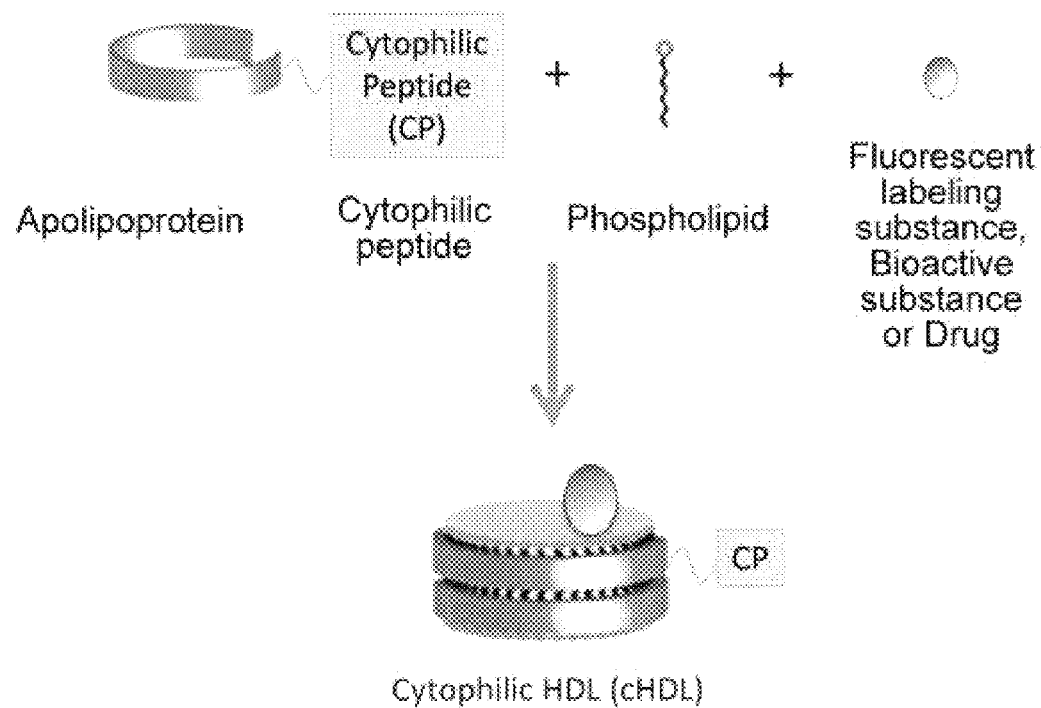
FIG. 2 is an illustration schematically showing the structure of a high-density lipoprotein (cHDL) to which the cytophilic peptide of the present invention is bound (for example, fused).

The cytophilic peptide (CP) binds (for example, fuses) to the high-density lipoprotein of the present invention (HDL) to form a cytophilic peptide-bound high-density lipoprotein (cHDL). The cytophilic peptide (CP) preferably binds (for example, fuses) onto an apolipoprotein, and more preferably binds (for example, fuses) to the C terminal of an apolipoprotein. The binding method used herein may be a chemical synthetic approach (for example, coupling method) or a biological approach (for example, genetic engineering method). The, "fusion" used herein refers to artificial binding of the cytophilic peptide and a high-density lipoprotein (HDL) through a genetic engineering method, e.g., by preparing a transforming (fusion) gene. The functional group and position used for fusion on a high-density lipoprotein may be appropriately changed depending upon the cytophilic peptide to be fused. A structure of the high-density lipoprotein (cHDL) having the cytophilic peptide of the present invention fused thereto is schematically shown in FIG. 2.

An optional component, "fluorescent labeling substance" used herein refers to a substance serving as a fluorescent label. In the present invention, the fluorescent label is a labeling substance which can be used as a fluorescent label to a protein, enclosed and contained in the high-density lipoprotein of the present invention (cHDL). A chemically synthetized substance and a fluorescent protein are included; however, a chemically synthetized substance is preferable. As the functional group which reacts with a protein, e.g., a N-hydroxysuccinimide (NHS) ester (reactive to amine), isocyanate (reactive to amine), maleimide (reactive to SH) and hydrazide (reactive to aldehyde) can be used. Fluorescent labeling substances having these functional groups can be used. As the fluorescent labeling reagent, a commercially available one can be used or the fluorescent labeling reagent may be prepared by chemical synthesis or biological synthesis. For example, chemically synthesized substances such as fluorescein, rhodamine, coumarin-6, Cy-dye (R), Alexa Fluor (R) and HiLyte Fluor (R), and fluorescent proteins such as phycoerythrin (PE) and allophycocyanin (APC) are included; however, the fluorescent labeling agent is not limited to them.

An optional component, a "bioactive substance" used herein refers to a substance having properties acting on a physiological regulatory function in a living body, for example, a substance acting on the physiological regulatory function in the eye (for example, the posterior eye segment). Examples of the bioactive substance can include decongestant components usually used in ophthalmic compositions (for example, α-adrenergic agonist, more specifically epinephrine hydrochloride, ephedrine hydrochloride), ophthalmic muscle regulatory components (for example, cholinesterase inhibitor, more specifically tropicamide), anti-inflammatory drug components or astringent drug components (for example, zinc sulfate, indomethacin, bromfenac sodium), antihistamine drug components or antiallergic drug components (for example, diphenhydramine hydrochloride, chlorpheniramine maleate), vitamins (for example, retinol palmitate, ascorbic acid), amino acids (for example, sodium aspartate, sodium glutamate), acid mucopolysaccharides (for example, sodium chondroitin sulfate), and local anesthetic components (for example, chlorobutanol, procaine hydrochloride).

As an optional component, "drug" used herein, for example, drugs effective for diagnosis, prevention or treatment of ocular diseases can be included. Examples of the drug include drugs effective for diagnosis, prevention or treatment of a disease of the anterior eye segment, a disease of the posterior eye segment and a disease of the external eye segment. More specifically, "drugs effective for diagnosis, prevention or treatment of diseases of the posterior eye segments" described later can be included.

The high-density lipoprotein of the present invention (HDL) (for example, rHDL) and cytophilic peptide-bound high-density lipoprotein (cHDL) further contain one molecule or more of at least one compound selected from a fluorescent labeling substance, a bioactive substance or a drug, per molecule of the protein to thereby form a complex.

In the cytophilic peptide-bound high-density lipoprotein (cHDL) of the present invention, the ratios of components to be contained relative to a cHDL-containing solution are as follows:

an apolipoprotein: for example, about 0.01 to 0.5 µmoL/L, typically about 0.05 to 0.1 µmoL/L, a phospholipid: for example, about 0.5 to 250 µmoL/L, typically about 2.5 to 20 µmoL/L and a cytophilic peptide fused to the apolipoprotein in an equivalent molar ratio.

at least one compound selected from a fluorescent labeling substance, a bioactive substance or a drug may be optionally contained, for example, in a ratio of about 0.01 to 25 µmoL/L, typically about 0.02 to about 10 µmoL/L, about 0.05 to about 2 µmoL/L (for example, 0.03 µmoL/L, 0.05 µmoL/L, 0.1 µmoL/L, 0.2 µmoL/L).

As an embodiment of the cytophilic peptide-bound high-density lipoprotein (cHDL) of the present invention, for example, a phospholipid (about 0.1 to 100 mg/mL, about 1 to 50 mg/mL, about 2 to 20 mg/mL, typically about 5 mg/mL), and optionally at least one compound selected from a fluorescent labeling substance, a bioactive substance or a drug (about 0.001 to 1 mg/mL, about 0.01 to 0.5 mg/mL, about 0.02 to 0.1 mg/mL, typically about 0.05 mg/mL) per apolipoprotein (1 mg/mL) are contained. As a preferable embodiment, for example, a phospholipid (about 5 mg/mL), and optionally at least one compound selected from a fluorescent labeling substance, a bioactive substance or a drug (about 0.05 mg (50 µg)/mL) per apolipoprotein (1 mg/mL) are contained.

The "carrier for delivering a drug to the posterior eye segment" used herein refers to a carrier for use in delivering a drug to the posterior eye segment. The high-density lipoprotein (cHDL) having a cytophilic peptide bound (for example, fused) thereto according to the present invention can transfer a highly concentrated drug to the retina cell tissue by enclosing the drug, which is difficult to deliver to the posterior eye segment by itself due to the presence of the intraocular blood hydraulic barrier and the blood retinal barrier, into the high-density lipoprotein (cHDL) having the cytophilic peptide bound (for example, fused) thereto. In particular, if a drug effective for diagnosis, prevention or treatment of a disease of the posterior eye segment is delivered, the diagnosis, prevention or therapeutic effect for a disease of the posterior eye segment can be greatly improved.

The high-density lipoprotein (cHDL) having a cytophilic peptide bound (for example, fused) thereto according to the present invention is useful as a carrier for delivering a drug to the posterior eye segment and thus can construct "the system for delivering a drug to the posterior eye segment".

The "pharmaceutical composition for a disease of the posterior eye segment" used herein refers to a pharmaceutical composition for diagnosing, preventing or treating a disease of the posterior eye segment which comprises, as components, a high-density lipoprotein (cHDL) having a cytophilic peptide bound (for example, fused) thereto according to the present invention as mentioned above, a drug effective for diagnosis, prevention or treatment of a disease of the posterior eye segment which is contained (for example, enclosed) in the high-density lipoprotein, and optionally pharmaceutically acceptable additive(s).

The "drug effective for diagnosis, prevention or treatment of a disease of the posterior eye segment" used herein refers to those mentioned below, but is not limited to them. Examples thereof include diagnostic, prophylactic (or preventing) or therapeutic agents for age-related macular degeneration, diagnostic, prophylactic or therapeutic agents for diabetic retinopathy, diagnostic, prophylactic or therapeutic agents for diabetic macular edema, diagnostic, prophylactic or therapeutic agents for retinal artery obstruction or retinal vein obstruction, diagnostic, prophylactic or therapeutic agents for uveitis, diagnostic, prophylactic or therapeutic agents for retinal degenerative disease, diagnostic, prophylactic or therapeutic agents for retinal detachment, diagnostic, prophylactic or therapeutic agents for glaucoma, diagnostic, prophylactic or therapeutic agents for cataract, and diagnostic, prophylactic or therapeutic agents for vitreous cloudiness. Specific examples thereof include, but are not limited to, vascular endothelial growth factor (VEGF) inhibitors (for example, VEGF antibody, VEGF aptamer, siRNA), steroid preparations (for example, dexamethasone, betamethasone, fluorometholone, prednisolone), non-steroid preparations (for example, indomethacin, bromfenac, diclofenac sodium), prostaglandin preparations (for example, latanoprost, tafluprost), pirenoxine, glutathione, memantine, epinephrine, pilocarpine hydrochloride, carbachol, dorzolamide hydrochloride, acetazolamide, timolol maleate, carteolol hydrochloride, betaxolol hydrochloride, bunazosin hydrochloride, isopropyl unoprostone, pranoprofen, aspirin and Pazopanib. For example, a drug for suppressing an intraocular neovascularization blood vessel (for example, choroidal neovascular vessel) is mentioned. Preferably, a diagnostic, prophylactic or therapeutic agent for age-related macular degeneration, diabetic retinopathy, diabetic macular edema, or retinal artery or vein obstruction is mentioned.

As the "pharmaceutically acceptable additive(s)" used herein, other than the aforementioned components, various active ingredients or medicinal components (including pharmacologically active ingredients and physiologically active ingredients) and additives (for example, a buffering agent, a tonicity agent, a pH adjustor, an antiseptic/preservative, a stabilizer, a thickener, a chelating agent, a surfactant, a fragrance) may be contained in combination, as long as the advantageous effects of the present invention are not inhibited. These components can be optionally added within concentration ranges in which problems such as eye irritation do not occur. Although the types of components are not particularly limited, examples of the components include a buffering agent (for example, sodium phosphate), a tonicity agent (for example, sodium chloride), a pH adjustor (for example, boric acid), an antiseptic/preservative (for example, benzalkonium chloride), a stabilizer (for example, mannitol), a thickener (for example, sodium alginate), a chelating agent (for example, sodium edetate), a surfactant (for example, polyoxyethylene sorbitan monooleate) and a fragrance (for example, menthol).

The pharmaceutical composition of the present invention may be used in the dosage form such as an eye-drop, an eye ointment, a nose drop, an ear drop and an injection, and an eye-drop is preferable.

The form "for ocular instillation" used herein refers to a noninvasive dosage form such as an eye-drop. In the eye-drop, a dosage form thereof can be determined depending upon the solubility of a drug to water and the stability of the drug in an aqueous solution, from an aqueous eye-drop, an eye-drop required dissolution in use, a suspension eye-drop, or an oily eye-drop/eye ointment. The eye-drops may comprise pharmaceutically acceptable additives for use in ocular instillation such as a buffering agent, a tonicity agent, a pH adjuster, a surfactant, a stabilizer and a preservative; however, the additives are not limited to them. The pH of an eye-drop is not limited as long as it falls within the range acceptable for ophthalmic preparations, and preferably falls within the usual range of 4 to 8. Examples of the buffering agent include a phosphate (for example, sodium phosphate) and an acetate (for example, sodium acetate). Examples of the tonicity agent include an inorganic salt such as sodium chloride and glycerin such as concentrated glycerin. Examples of the pH adjuster include an organic acid such as boric acid. Examples of the surfactant include a nonionic surfactant (for example, a polyoxyethylene sorbitan fatty acid ester such as polyoxyethylene sorbitan monooleate), an amphoteric surfactant (for example, a glycine surfactant such as an alkyldiaminoethylglycine and an acetic acid betaine surfactant such as lauryldimethylaminoacetic acid betaine), an anionic surfactant (for example, a sulfonate such as sodium tetradecenesulfonate and alkyl sulfate such as sodium lauryl sulfate) and a cationic surfactant (for example, an alkyl quaternary ammonium salt such as benzalkonium chloride) and a nonionic surfactant is preferable. Examples of the stabilizer include an organic acid salt (for example, sodium citrate and mannitol). Examples of the preservative include benzalkonium chloride and paraben.

The "system for delivering a drug to the posterior eye segment" used herein is constructed by combining the high-density lipoprotein (cHDL) to which a cytophilic peptide is bound (for example, fused) according to the present invention and which serves as a carrier for delivering a drug to the posterior eye segment, and a drug effective for diagnosis, prevention or treatment of a disease of the posterior eye segment.

It is possible to diagnose, prevent or treat a disease of the posterior eye segment by applying the system for delivering a drug to the posterior eye segment to patients having the disease of the posterior eye segment or having a risk of developing the disease, or by conducting a method for administering the pharmaceutical composition for the disease of the posterior eye segment.

The "disease of the posterior eye segment" used herein refers to a disease in the intraocular vitreous body, retina, choroid, sclera or optic nerve. Examples thereof include, but are not limited to, age-related macular degeneration, diabetic retinopathy, diabetic macular edema, retinal artery or vein obstruction, uveitis, retinal degenerative disease (for example, retinitis pigmentosa), degenerative myopia, macular hole, macular epithelium, retinal detachment, glaucoma, cataract and vitreous cloudiness. For example, a disease caused by the intraocular neovascularization blood vessel (for example, choroidal neovascular vessel) is included. Preferably, age-related macular degeneration, diabetic retinopathy, diabetic macular edema and retinal artery or vein obstruction are included.

Next, a method for preparing the high-density lipoprotein (cHDL) having the cytophilic peptide bound (for example, fused) thereto according to the present invention will be described; however, the method is not limited to the following ones.

An object of the present invention is directed to a method for preparing a high-density lipoprotein (cHDL) having a cytophilic peptide bound (for example, fused) thereto, which comprises i) fusing a cytophilic peptide to an apolipoprotein by a genetic engineering technique to obtain a fusion protein;

ii) blending a liposome containing a phospholipid and, if necessary at least one compound selected from a fluorescent labeling substance, a bioactive substance or a drug, with the fusion protein obtained above to produce a crude cHDL (Spontaneous interaction method); or mixing a cholate micelle with the fusion protein obtained above (for example, mixing at a phase transition temperature of a phospholipid) not via formation of a liposome to produce a crude cHDL (cholate-dialysis method); and iii) removing unreacted liposome, phospholipid micelle, and/or apolipoprotein by an ultracentrifugation method to purify the crude cHDL.

Examples of the genetic engineering technique include DNA editing using methylase and DNA polymerase I/DNA ligase and a polymerase chain reaction (PCR) method. More specifically, a TAT peptide gene having a Xba I recognition sequence added to both 5' and 3' ends is inserted to a restriction enzyme Xba I recognition site of *Escherichia coli* expression vector, pCOLD I, by use of DNA ligase. DNA sequence analysis is carried out to select a vector having the TAT peptide gene in the forward direction. Subsequently, a gene having a restriction enzyme Kpn I recognition sequence added to the 5' end of a N-terminal 43 amino acid deficient apoA-I gene and a restriction enzyme Pst I recognition sequence to the 3' end thereof is prepared by a PCR method and inserted in the interval between Kpn I and Pst I recognition sites of the above pCOLD I by use of DNA ligase. By the above operation, a polypeptide gene having the TAT peptide fused to the C terminal side of the N terminal 43 amino acid deficient apoA-I is prepared.

In a preferable embodiment, the present invention provides a cytophilic peptide-bound high-density lipoprotein (cHDL), which comprises a) a high-density lipoprotein (HDL) containing an apolipoprotein and a phospholipid, wherein the apolipoprotein is at least one apolipoprotein selected from the group consisting of apolipoprotein A-I and a genetically modified apolipoprotein A-I thereof, and the phospholipid is a glycerophospholipid of a fatty acid group having 12 to 18 carbon atoms;

b) a cytophilic peptide (CPP) selected from the group consisting of basic cell membrane permeable peptides; and c) optionally at least one compound selected from the group consisting of a fluorescent labeling substance, a bioactive substance or a drug, and which has a particle size of less than 100 nm in diameter (for example, 10 to 20 nm in diameter).

In another preferable embodiment, the present invention provides a pharmaceutical composition for diagnosis, prevention or treatment of at least one disease selected from the group consisting of age-related macular degeneration, diabetic retinopathy, diabetic macular edema and retinal artery or vein obstruction, comprising 1) a cytophilic peptide-bound high-density lipoprotein (cHDL),
   which comprises
   a) a high-density lipoprotein (HDL) containing an apolipoprotein and a phospholipid, wherein
   the apolipoprotein is at least one apolipoprotein selected from the group consisting of apolipoprotein A-I and a genetically modified apolipoprotein A-I thereof, and
   the phospholipid is a glycerophospholipid of a fatty acid group having 12 to 18 carbon atoms;
   b) a cytophilic peptide selected from the group consisting of basic cell membrane permeable peptides; and
   c) at least one compound appropriately selected from a compound which serves as a drug for suppressing intraocular neovascularization (for example, choroidal neovascularization), or a diagnostic, prophylactic or therapeutic agent for a disease selected from the group consisting of age-related macular degeneration, diabetic retinopathy, diabetic macular edema and retinal artery or vein obstruction, and,
   which has a particle size of less than 100 nm in diameter (for example, 10 to 20 nm in diameter), and 2) a pharmaceutically acceptable additive.

The content ratio of typical components in preparing the cytophilic peptide-bound high-density lipoprotein (cHDL) according to the present invention is as follows.

A fusion protein is prepared by adding the cytophilic peptide in an equivalent molar ratio relative into the high-density lipoprotein (HDL) before fusing.

Next, cHDL is prepared by adding a phospholipid in a supply (or adding) amount which is several to several thousands of times, several tens to several hundreds of times, for example about 5 times to about 2000 times, about 20 times to about 500 times, about 30 times to about 200 times as large as one mole of the high-density lipoprotein (HDL) before fusing.

The particle size of the high-density lipoprotein (cHDL) having the cytophilic peptide bound (for example, fused) as prepared above can be controlled to fall into the size range of fine particles by e.g., an ultrasonic irradiation method, a freezing/thawing method and/or a homogenization method; however, the controlling method is not limited to these methods. The resultant particle size of the protein can be determined by measuring it by a predetermined method. The particle size can be determined by measuring it by a commercially available Zetasizer.

EXAMPLES

The present invention will be further more specifically described by way of Examples; however, the present invention is not limited to these Examples.

Example 1

A high-density lipoprotein (HDL) was prepared by the following method.
Preparation of Cytophilic HDL (cHDL)
(Method)
A fusion protein was prepared by ligating a TAT (Transactivator of transcription protein) peptide having a cytophilic property to the C terminal of genetically modified apoA-I. To the apoA-I fusion protein, a liposome composed of a phospholipid, i.e., dimistryl phosphatidylcholine (DMPC) and a fluorescent labeling substance, i.e., coumarin-6 and having a particle size as small as about 100 nm were mixed to prepare cHDL (Spontaneous interaction method). In order to remove an unreacted liposome, phospholipid micelle, and an apolipoprotein binding to neither the phospholipid nor a fluorescent substance, from the mixture of genetically modified apoA-I and the liposome, cHDL was purified by an ultracentrifugation method.

As a comparative control, recombinant HDL (rHDL) not containing TAT peptide was prepared in the same manner. As a comparative control, distearoyl phosphatidylcholine (DSPC) of ssLip (submicron sized small uni-lamella vesicle) of a liposome was prepared in accordance with a method described in International Publication No. WO 2009/107753. With respect to each of the HDL obtained above and DSPC prepared, the contents of protein, phospholipid and coumarin-6 in the composition, and the particle size and surface potential thereof were examined. Protein was examined by Lowry method. Phospholipid was examined by C test (C test Wako (R)). Coumarin-6 was examined by fluorescence spectroscopy using a fluorescence spectrophotometer, FluoroMax. The particle size and surface charge state were examined by a dynamic light scattering method (DLS) as a volume average diameter (MV) and a zeta potential, respectively.

(Results)

HDLs having a particle size (diameter) as small as 10 to 20 nm were successfully obtained by a Spontaneous interaction method and an ultracentrifugation method. The size of each HDL and the concentrations of protein, phospholipid and coumarin-6 constituting the HDL and zeta potential are shown in the table below.

TABLE 1

| | Protein (μmoL/mL) | Phospholipid (μmoL/mL) | Coumarin-6 (μmoL/mL) | Volume average diameter (nm) | Zeta potential (mV) |
|---|---|---|---|---|---|
| cHDL | 0.105 | 30.48 | 0.1 | 14.58 | −3.16 |
| rHDL | 0.087 | 26.15 | 0.1 | 13.92 | −9.06 |
| DSPC ssLip | | 3.92 | 0.1 | 112.5 | −16.2 |

Protein was examined by Lowry method. Phospholipid was examined by C test (C test Wako (R)). Coumarin-6 was examined by fluorescence spectroscopy using a fluorescence spectrophotometer, FluoroMax. The volume average diameter and zeta potential were examined by a dynamic light scattering method (DLS).

Example 2

Figure 3:
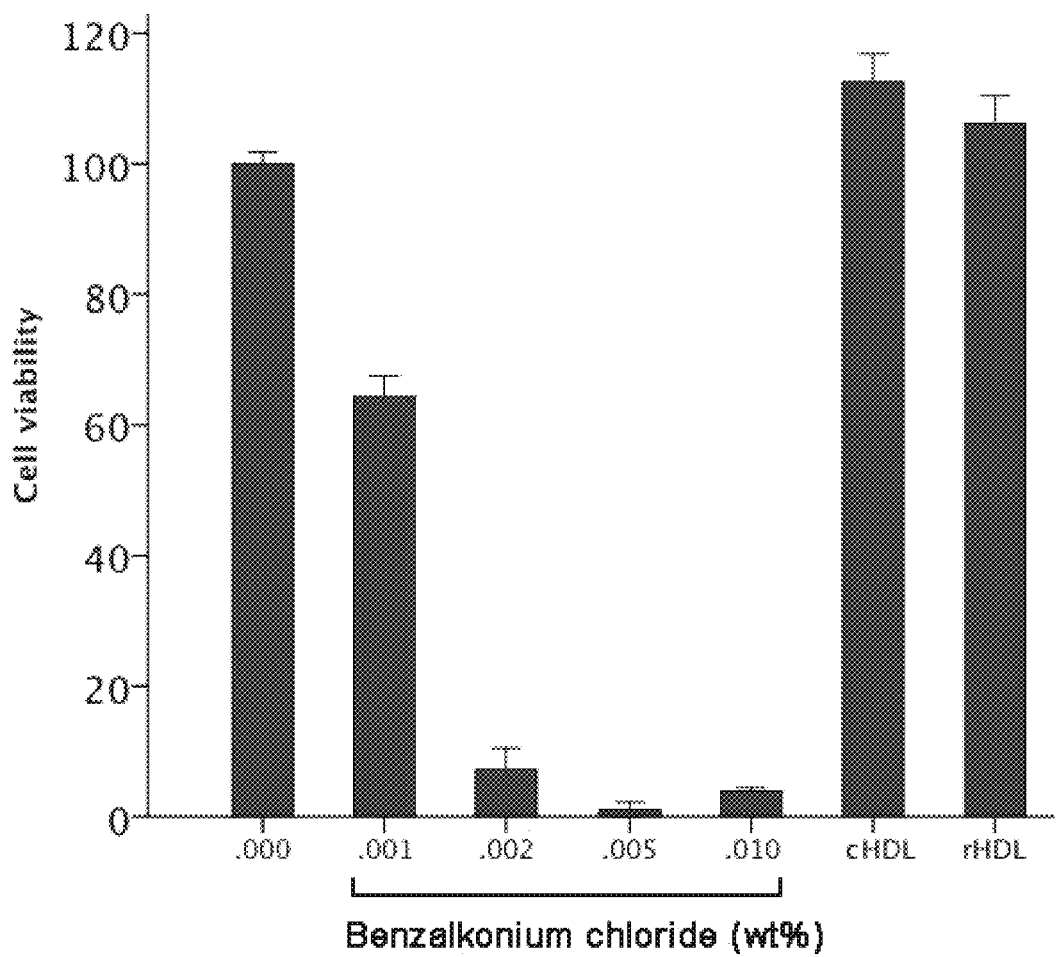
FIG. 3 is a graph showing the results of a cytotoxicity test. In the graph, the results of comparing cHDL or rHDL with a HBSS/HEPES solution as a negative control, or benzalkonium chloride as a positive control are shown.

Next, a membrane toxicity test using individual HDLs produced was carried out.
Toxicity Evaluation of cHDL
(Method)
A cytotoxicity test using the human cornea cultured-cells was carried out in order to examine corneal toxicity of individual HDLs obtained. The test was carried out for cHDL, rHDL and a comparative control, benzalkonium chloride by a colorimetry method for measuring enzyme activity. CCK-8 test using CCK-8 (Cell Counting Kit-8) as a detection reagent was adopted.
(Results)
Both cHDL and rHDL showed cell viabilities, which were the equal to or higher than that of a negative control (typical example), i.e., an HBSS/HEPES solution, and showed cytotoxicities, which were significantly lower than that of a positive control (typical example), i.e., benzalkonium chloride (a preservative contained in commercially available eye-drops) (FIG. 3).

Example 3

Efficiency of the cHDLs obtained in reaching the retina was examined.
Efficiency of cHDLs in Reaching the Retina
(Method)

Mice C57/B6 were used as an experimental animal. Each drop (3 μL) of cHDL, rHDL or DSPC liposome of 100 nm in particle size, each containing a coumarin-6 concentration of 0.1 μmoL/mL was placed in an eye surface of a mouse. Thirty(30) minutes later, the eyeball was removed, frozen and then sliced to obtain a frozen specimen. The retina of the frozen specimen was observed and the fluorescence intensity of the retinal inner layer was observed by a confocal microscope. The results were compared.
(Results)

Figure 4:
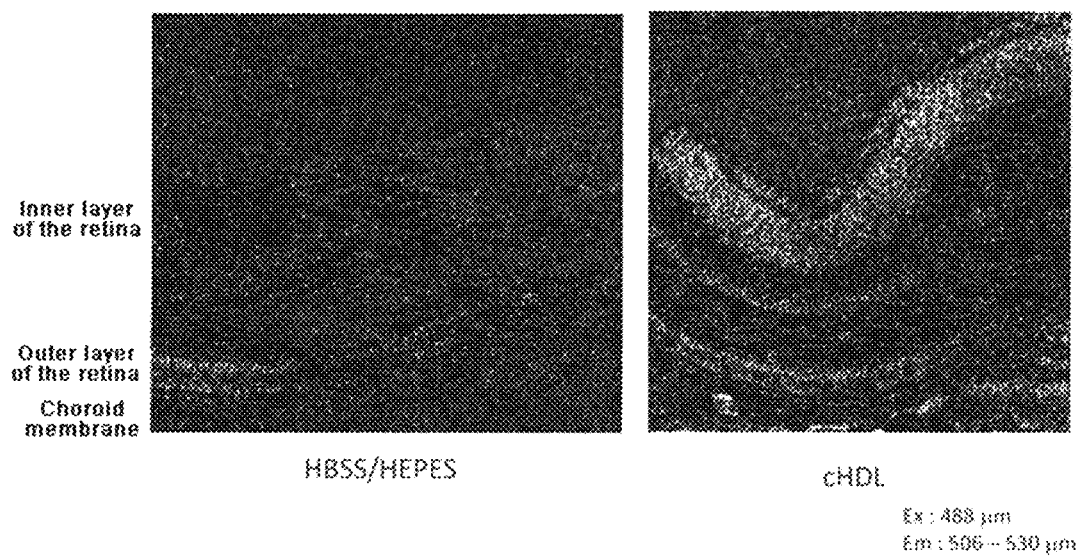
FIG. 4 shows the observation results by a fluorescent microscopy, showing the results of a delivery confirmation test to the posterior eye segment cell tissue. In the figure, the comparison results of cHDL and a buffer 30 minutes after ocular instillation are shown.

In the observation by a confocal microscope, fluorescence, which was not observed in a coumarin-6-free HBSS/HEPES buffer ocular instillation group, was observed in the retinal inner layer in the cHDL ocular instillation group (FIG. 4).

Figure 5:
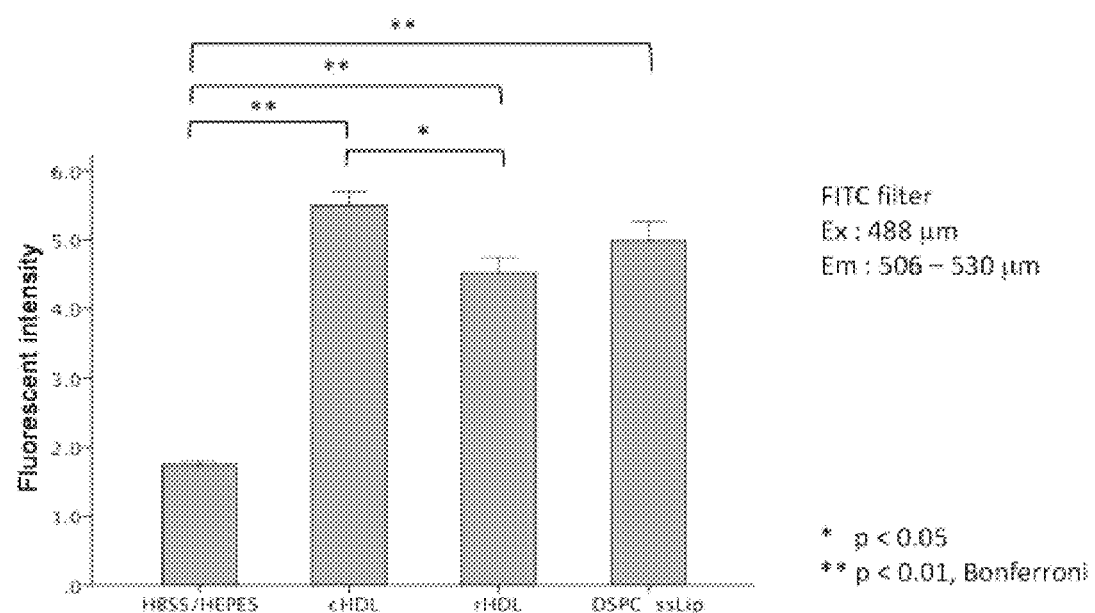
FIG. 5 is a graph showing digitalized fluorescence intensity resulting from a delivery confirmation test to the posterior eye segment cell tissue. In the graph, the comparison results of cHDL, rHDL, an HBSS/HPES solution as a negative control and a small size liposome, i.e., DSPC ssLip (submicron sized small uni-lamella vesicle) as a positive control are shown.

These fluorescence intensity results with respect to cHDL, rHDL, the HBSS/HPES solution as a negative control, and the liposome DSPC ssLip as a positive control were digitalized (FIG. 5). Compared to the HESS/HEPES ocular instillation group, the fluorescence intensity of the retinal inner layer was improved in all of ocular instillation groups for the cHDL, rHDL, and DSPC liposome (100 nm in particle size). In addition, cHDL showed high fluorescence intensity, compared to either one of rHDL and DSCP liposome (100 nm in particle size). From the results, it was suggested that HDL of the present invention (for example, rHDL) can deliver coumarin-6 significantly to the retinal inner layer. In particular, it was suggested that cHDL having a cytophilic peptide bound thereto can deliver coumarin-6 at an extremely high degree to the retina.

Example 4

As a model test for the system for delivering a drug to the posterior eye segment, a neovascularization model test was carried out in accordance with the following manner.
Model Test of the System for Delivering a Drug to the Posterior Eye Segment (e.g., Neovascularization Model)

The retina of each of 6 to 8 weeks-old C57BL6 mice was irradiated with argon laser to produce choroidal neovascular blood vessel. Immediately after the laser irradiation, an eye-drop solution was placed three times per day in a dose of 3 μL for a week. A week later, the eyeballs were removed. The choroidal neovascular blood vessels were stained in accordance with an immunostaining method. The areas of the choroidal neovascular vessels were measured by a flat mount method under a confocal microscope to determine a therapeutic effect. 1) Samples obtained by mixing Pazopanib (1 mg) with each of a cHDL solution (1 mL) having an apolipoprotein concentration of 1 mg/mL and a cHDL-free buffer solution (1 mL) (FIG. 6) were mutually compared; and 2) A solution of cHDL enclosing Pazopanib in an equivalent mole as an apolipoprotein and a solution of cHDL enclosing no Pazopanib (both had an apolipoprotein concentration: 1.5 mg/mL) (FIG. 7), were mutually compared. The solution of cHDL enclosing Pazopanib was prepared by using Pazopanib in place of coumarin-6 in Example 1.

Figure 6:
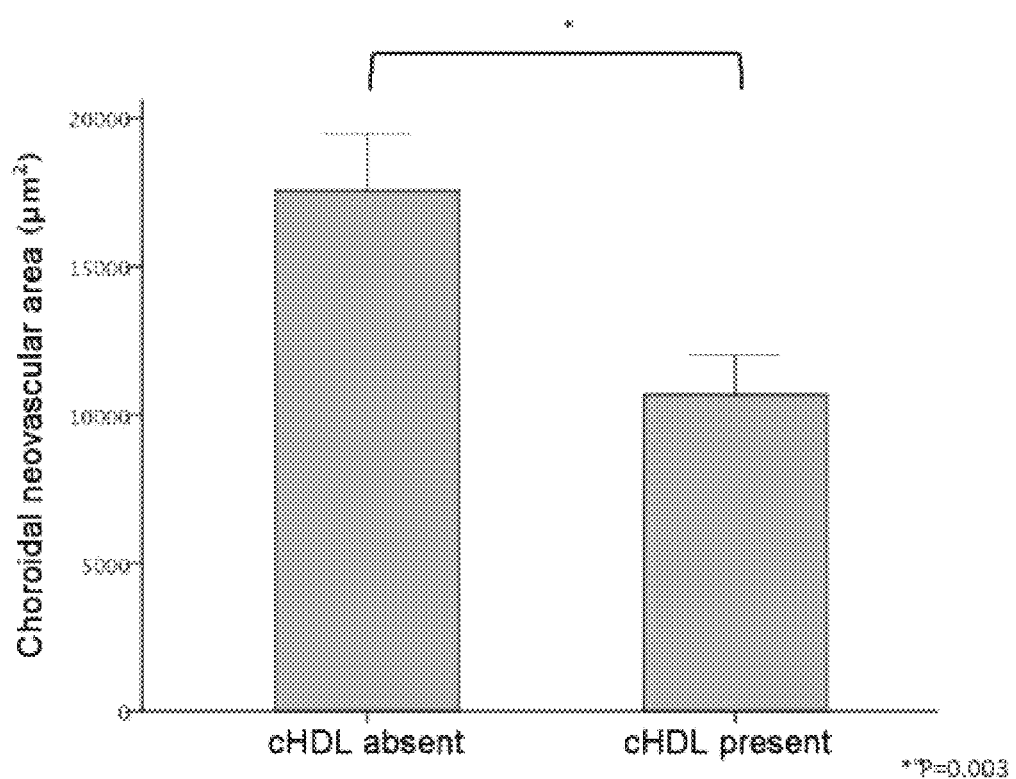
FIG. 6 is a graph showing the results of suppression of a choroidal neovascular area after ocular instillation in the presence or absence of cHDL enclosing a drug in a neovascularization model test by a system for delivering a drug to the posterior eye segment. In the graph, the comparison results of the case where a drug Pazopanib is enclosed in cHDL and the case of Pazopanib used as it is (not enclosed in cHDL) are shown.
Figure 7:
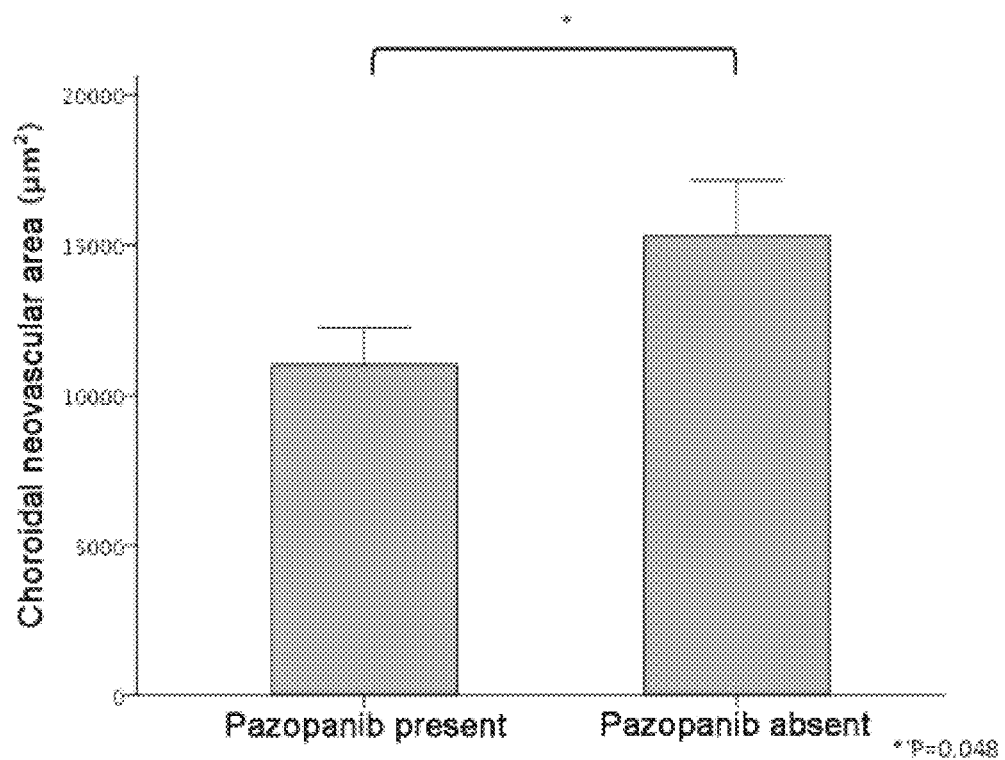
FIG. 7 is a graph showing the results of suppression of a choroidal neovascular area after ocular instillation in the presence or absence of a drug enclosed in cHDL in a neovascularization model test by a system for delivering a drug to the posterior eye segment. In the graph, the comparison results of the case where a drug Pazopanib is enclosed in cHDL and the case of Pazopanib is used as it is (not enclosed in cHDL) are shown.

As a result, in either case, the area of choroidal neovascular blood vessel was decreased by ocular instillation of the solution of cHDL enclosing a drug. It was suggested that a drug having a neovascularization inhibitory action reaches a diseased part by means of enclosing in cHDL (FIG. 6, FIG. 7). This suggests that Pazopanib as a drug reaches the posterior eye segment and effectively suppress neovascularization.

Example 5

To study the roles of phospholipids different in type in delivering a drug to the retina, cytophilic HDLs (cHDL) were prepared by using different types of phospholipids and efficiency of them in reaching the retina was examined.
1) Preparation of Cytophilic HDL (cHDL)
(Method)

High-density lipoproteins (cHDL) were prepared by using different types of phospholipids (more specifically, three types of phospholipids, DMPC, DPPC and DSPC) in accordance with the following method.

More specifically, a micelle composed of coumarin-6, a phospholipid and cholate were prepared. The micelle and apoA-I were mixed at the phase transition temperature of a phospholipid (cholate-dialysis method) to prepare high-density lipoproteins (cHDL). The phase transition temperatures of phospholipids are as follows: DMPC: 24° C., DPPC: 40-41° C. and DSPC: 55° C.

The concentration of coumarin-6 was 0.05 μmol/ml, which was used in all samples. The cHDLs obtained were purified by an ultracentrifugation method in accordance with the method of Example 1.

With respect to each of the cHDLs obtained above, the contents of protein, phospholipid and coumarin-6 in the composition and the particle size were examined in accordance with the method of Example 1.
(Results)

cHDLs having a particle size (diameter) as small as 10 to 20 nm were obtained by a Spontaneous interaction method and an ultracentrifugation method. The particle size of each of the cHDLs and the concentrations of components: protein, phospholipid and coumarin-6 are as shown in Table 2 below.

TABLE 2

| | Protein (μmol/ml) | Phospholipid (μmol/ml) | Coumarin-6 (μmol/ml) | Volume average diameter (nm) |
| --- | --- | --- | --- | --- |
| DMPC-case | 0.167 | 24.88 | 0.05 | 12.74 |
| DPPC-case | 0.097 | 15.34 | 0.05 | 15.97 |
| DSPC-case | 0.130 | 12.96 | 0.05 | 15.05 |

2) Efficiency of cHDL in Reaching the Retina
(Method)

Efficiency of cHDLs produced above in reaching to the retina was examined.

More specifically, the fluorescence intensity in the retinal inner layer was observed by a confocal microscope in the same manner as in Example 3 and the results were compared.

(Results)

Figure 8:
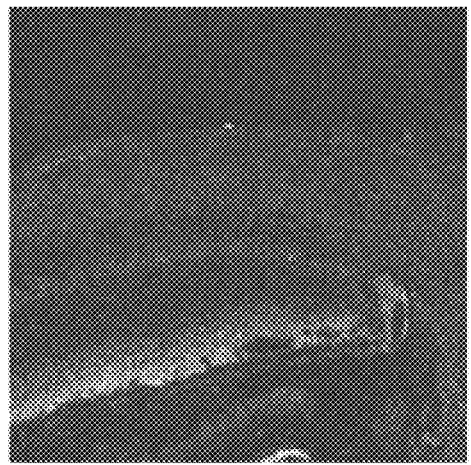
FIG. 8 shows observation results by a fluorescent microscopy, showing the results of a delivery confirmation test to the posterior eye segment cell tissue on cHDL in the case where DMPC, DPPC or DSPC was used as a phospholipid.
Figure 8:
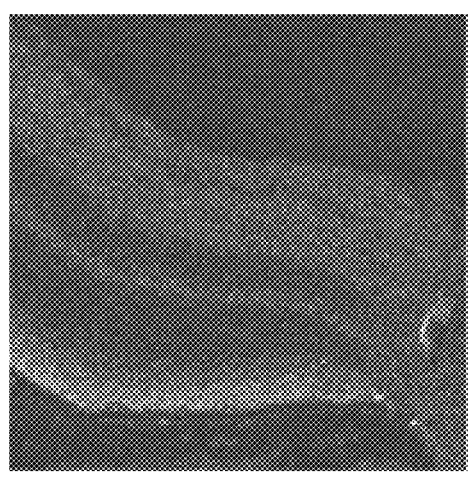
Figure 8:
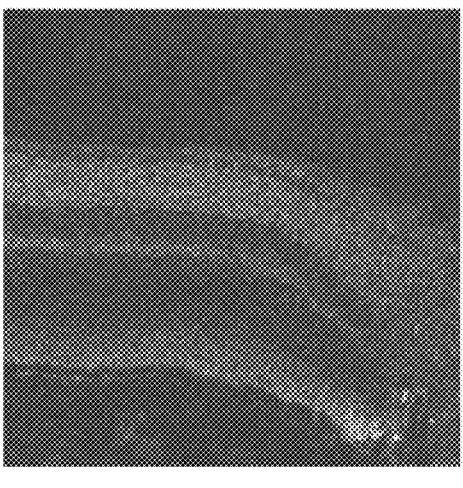

The fluorescence intensities in the retinal inner layers observed by a confocal microscope were compared. The results are shown in FIG. 8. The fluorescence intensity increased in the order of DSPC>DPPC>DMPC.

These resultant fluorescence intensities were digitalized in accordance with the method of Example 3 (FIG. 9).

From the results, it was suggested that the HDL of the present invention can deliver coumarin-6 significantly to the retinal inner layer, and that particularly a cytophilic peptide-bound cHDL can deliver coumarin-6 to the retina at an extremely high degree. It was also suggested that as the number of carbon atoms of the alkyl group in the acyl group of a sphingophospholipid increases, in other words, as the chain length of the phospholipid increases, the efficiency of the phospholipid in reaching the retina can be improved.

Example 6

Cytophilic HDLs (cHDL) Using Various Cell Membrane Permeable Peptides (CPP)

To study the roles of cell membrane permeable peptides (CPP) different in type in delivering a drug to the retina, cytophilic HDLs (cHDL) were prepared by using different types of cell membrane permeable peptides and the efficiency of them in reaching to the retina was examined.

1) Preparation of Cytophilic HDL (cHDL)

(Method)

Proteins fused to N-terminal 43 amino acid deficient apoA-I were prepared by using different CPPs (more specifically, three types of CPPs: TAT peptide, penetratin (PEN) peptide, polyarginine (R8)) in accordance with the same genetic engineering technique as aforementioned herein. Subsequently, cHDL composed of DSPC and coumarin-6 was prepared in the same manner as in Example 5. The concentration of coumarin-6 was 0.03 µmol/ml, which was used in all samples. The cHDLs obtained were purified by an ultracentrifugation method in accordance with the method of Example 1.

With respect to each of the cHDLs obtained above, the contents of protein, phospholipid and coumarin-6 in the composition and the particle size and surface potential were examined in accordance with the method of Example 1.

(Results)

cHDLs having a particle size (diameter) as small as 10 to 20 nm were obtained by a Spontaneous interaction method and an ultracentrifugation method. The particle sizes of the cHDLs, the concentrations of the protein, phospholipid and coumarin-6 constituting them and the zeta potential are as shown in Table 3 below.

TABLE 3

|  | Protein (µmol/ml) | Phospholipid (µmol/ml) | Coumarin-6 (µmol/ml) | Volume average diameter (nm) | Zeta potential (mV) |
| --- | --- | --- | --- | --- | --- |
| CPP-free case | 0.135 | 16.80 | 0.03 | 17.55 | −14.4 |
| TAT case | 0.128 | 16.98 | 0.03 | 15.38 | −7.56 |
| PEN case | 0.133 | 26.21 | 0.03 | 19.51 | −7.01 |
| R8 case | 0.119 | 19.04 | 0.03 | 19.42 | −4.75 |

2) Efficiency of cHDL in Reaching the Retina (Method)

Efficiency of cHDLs prepared above in reaching to the retina was examined.

More specifically, the fluorescence intensity in the retinal inner layer was observed by a confocal microscope in the same manner as in Example 3 and the results were compared.

(Results)

The fluorescence intensities of the retinal inner layers observed by a confocal microscope were compared. The results are shown in FIG. 10. The fluorescence intensity increased in the order of PEN>R8≥TAT>CPP.

These resultant fluorescence intensities were digitalized in accordance with the method of Example 3 (FIG. 11).

From the results, it was suggested that the HDL of the present invention can deliver coumarin-6 significantly to the retinal inner layer and that particularly a cytophilic peptide-bound cHDL can deliver coumarin-6 to the retina at an extremely high degree. In addition, it was suggested that PEN most improves the efficiency of cHDL in reaching to the retina.

Example 7

Concentration Dependency of Drug Delivery to the Retina

Concentration dependency of drug delivery to the retina was studied by using cHDL containing PEN peptide, DSPC and coumarin-6.

cHDL solutions were prepared so as to contain coumarin-6 in a concentration of 0.03 µmol/ml, 0.05 µmol/ml, 0.1 µm/ml and 0.2 µmol/ml, in the same manner as in Example 5 or 6. Then, the individual solutions were used in the same manner as in Example 3 and the fluorescence intensity values of retinal inner layers were compared. The results are shown in FIG. 12. It was found that as the concentration of coumarin-6 increases, the fluorescence intensity value tends to increase.

These results of fluorescence intensity were digitalized in accordance with the method of Example 3 (FIG. 13).

From the results, it was suggested that if the concentration of a drug contained in cHDL is high, the high-concentration drug can be delivered to the retina, and found that the concentration of a drug delivered to the retina depends on the concentration of the drug contained in the cHDL to be applied.

Example 8

Experiment for Comparing the cHDL of the Present Invention and a Conventional Carrier as a Drug Delivery Carrier Usefulness of cHDL according to the present invention as a drug-delivery carrier to the posterior eye segment was studied in comparison with a conventional carrier.

Pazopanib was selected as a drug. As a positive control carrier of Pazopanib, captisole generally used in clinical trials and small-size liposome (ssLip) used as a comparative subject in Example 3 were selected. Pazopanib-containing cHDL of the present invention having Pazopanib was compared to the above-mentioned carrier complexes containing Pazopanib for usefulness as a carrier.

More specifically, as the cHDL of the present invention, the cHDL prepared in the same manner as in Example 4, 2) was used. Whereas, as the above carrier to be compared, a comparative captisol solution was prepared by dissolving Pazopanib in a 7% captisol solution in the same manner as described in Literature 1 (Yafai et al. Eur J Pharmacol. 2011; 666: 12-8) and Literature 2 (National Publication of International Patent Application No. 2013-525501). Pazopanib was enclosed in the ssLip by mixing Pazopanib dissolved in DMSO with ssLip prepared in the same manner as in Example 1, and then purifying the mixture by removing Pazopanib not enclosed by a gel-filtration column to prepare a comparative ssLip solution.

In this experiment, in order to unify the concentrations of Pazopanib, the concentrations of individual samples were measured by ultra-high performance liquid chromatography (UPLC) in accordance with the methods described in Literature 3 (International Publication No. WO 2011-069053) and Literature 4 (Escudero-Ortiz et al. Ther Drug Monit. 2015; 37: 172-9). Using a Pazopanib standard solution known in concentration, the retention time in chromatography was checked and the peak area positioned at the retention time was measured. In this manner, a calibration curve was created. Also in individual samples, the peak areas positioned at the same retention time was measured. From the calibration curve, Pazopanib concentrations were obtained. The samples were appropriately diluted so as to obtain the same concentration.

These solutions prepared were placed in eyes of neovascularization model mice in accordance with the method described in Example 4 except that the number of ocular instillation times per mouse was changed to two times per day, and then, the effect for reducing the area of choroidal neovascular (CNV) blood vessel was examined.

The results are shown in FIG. 14. In the case where the cHDL of the present invention was used as a carrier, the area of the choroidal neovascular blood vessel was significantly reduced, compared to the case where any of captisole and ssLip was used (FIG. 14). From this, it was suggested that a drug having an inhibitory action on neovascularization effectively reaches the diseased part by means of enclosing in cHDL.

INDUSTRIAL APPLICABILITY

The high-density lipoprotein (cHDL) having a cytophilic peptide bound (for example, fused) thereto according to the present invention can deliver a compound (for example, a drug) contained therein to the posterior eye segment, attains high accumulation of the compound in the retina cells and has no cytotoxicity. Accordingly, it is possible to provide a novel drug delivery by ocular instillation by enclosing a drug in the cHDL and it is expected to efficiently diagnose, prevent and treat a disease of the posterior eye segment.

The invention claimed is:

1. A cytophilic peptide-bound high-density lipoprotein, comprising a high-density lipoprotein, a cytophilic peptide, and optionally a fluorescent labeling substance,
    wherein the cytophilic peptide is penetratin or polyarginine (R8);
    wherein the high-density lipoprotein consists of apolipoprotein and at least one kind of phospholipid selected from the group consisting of dimyristoylphosphatidylcholine (DMPC), dipalmitoylphosphatidylcholine (DPPC) and distearoylphosphatidylcholine (DSPC);
    wherein the apolipoprotein is at least one kind selected from the group consisting of apolipoprotein A-I, apolipoprotein A-II, apolipoprotein C, apolipoprotein E, and apolipoprotein A-I with an N-terminal deletion of 43 amino acids.

2. The cytophilic peptide-bound high-density lipoprotein according to claim 1, wherein the cytophilic peptide-bound high-density lipoprotein consists of
    a high-density lipoprotein consisting of apolipoprotein A-I, and distearoylphosphatidylcholine (DSPC), and penetratin.

3. The cytophilic peptide-bound high-density lipoprotein according to claim 1, having a particle size ranging from 10 to 20 nm in diameter.

4. The cytophilic peptide-bound high-density lipoprotein of claim 1, further comprising a fluorescent labeling substance selected from the group consisting of fluorescein, rhodamine, coumarin-6, Cy-dye, Alexa Fluor, HiLyte Fluor, phycoerythrin (PE) and allophycocyanin (APC).

5. A complex comprising the cytophilic peptide-bound high-density lipoprotein according to claim 1, which further comprises at least one molecule of at least one of compound selected from a fluorescent labeling substance, a bioactive substance or a drug, per molecule of the high-density lipoprotein.

6. A carrier for delivering a drug to the posterior eye segment comprising the cytophilic peptide-bound high-density lipoprotein according to claim 1.

7. The carrier for delivering a drug to the posterior eye segment according to claim 6, which comprises the cytophilic peptide-bound high-density lipoprotein, wherein the cytophilic peptide-bound high-density lipoprotein consists of
    a high-density lipoprotein consisting of apolipoprotein A-I, and distearoylphosphatidylcholine (DSPC), and penetratin.

8. A pharmaceutical composition for diagnosis, or treatment of a disease of the posterior eye segment, comprising the cytophilic peptide-bound high-density lipoprotein according to claim 1, a drug effective for diagnosis, or treatment of a disease of the posterior eye segment which is contained in the cytophilic peptide-bound high-density lipoprotein, and a pharmaceutically acceptable additive.

9. The pharmaceutical composition according to claim 8, which is used for ocular instillation.

10. The pharmaceutical composition for diagnosis, or treatment of a disease of the posterior eye segment according to claim 8, wherein the disease of the posterior eye segment is at least one disease selected from the group consisting of age-related macular degeneration, diabetic retinopathy, diabetic macular edema, glaucoma, retinal artery or vein obstruction, retinal degenerative disease, degenerative myopia, macular hole, macular epithelium, retinal detachment, cataract, vitreous opacity and uveitis.

11. The pharmaceutical composition for diagnosis, or treatment of a disease of the posterior eye segment according to claim 8,
    wherein the disease is at least one disease selected from the group consisting of age-related macular degeneration, diabetic retinopathy, diabetic macular edema and retinal artery or vein obstruction, and
    the drug is at least one compound selected from a compound which serves as a drug for suppressing choroidal neoangiogenesis or a diagnostic, or therapeutic agent for a disease selected from the group consisting of age-related macular degeneration, diabetic retinopathy, diabetic macular edema and retinal artery or vein obstruction.

12. The pharmaceutical composition according to claim 8, wherein the drug is Pazopanib.

13. The pharmaceutical composition according to claim 12, which is used for ocular instillation for diagnosis, or treatment of a disease of the posterior eye segment, which comprises
  the cytophilic peptide-bound high-density lipoprotein consisting of
    a high-density lipoprotein consisting of apolipoprotein A-I, and distearoylphosphatidylcholine (DSPC), and penetratin;
  Pazopanib, and
  a pharmaceutically acceptable additive.

14. The pharmaceutical composition which is used for ocular instillation for diagnosis, or treatment of a disease of the posterior eye segment according to claim 13, wherein the disease is at least one disease selected from the group consisting of age-related macular degeneration, diabetic retinopathy, diabetic macular edema, and retinal artery or vein obstruction.

15. A method for diagnosis or treatment of a disease of the posterior eye segment, which comprises administering the pharmaceutical composition according to claim 8 to a subject.

16. The method according to claim 15, which is administered by an ocular instillation.

17. A method for preparing the cytophilic peptide-bound high-density lipoprotein according to claim 1, comprising
  i) binding a cytophilic peptide to an apolipoprotein to obtain a bound protein;
  ii) a) blending a liposome containing a phospholipid, at least one compound selected from a fluorescent labeling substance, a bioactive substance or a drug, with the bound protein obtained in the above i) to produce a crude high-density lipoprotein having the cytophilic peptide bound thereto; or,
  b) mixing a cholate micelle obtained, with at least one compound selected from a bioactive substance or a drug to produce a crude high-density lipoprotein having the cytophilic peptide bound thereto; and
  iii) removing unreacted liposome, phospholipid micelle and/or apolipoprotein by an ultracentrifugation method to purify the crude high-density lipoprotein having the cytophilic peptide bound thereto.

18. A method for preparing the complex according to claim 5, comprising
  i) binding a cytophilic peptide to an apolipoprotein to obtain a bound protein;
  ii) a) blending a liposome containing a phospholipid, at least one compound selected from a fluorescent labeling substance, a bioactive substance or a drug, with the bound protein obtained in the above i) to produce a crude high-density lipoprotein having the cytophilic peptide bound thereto; or,
  b) mixing a cholate micelle obtained, with at least one compound selected from a bioactive substance or a drug to produce a crude high-density lipoprotein having the cytophilic peptide bound thereto; and
  iii) removing unreacted liposome, phospholipid micelle and/or apolipoprotein by an ultracentrifugation method to purify the crude high-density lipoprotein having the cytophilic peptide bound thereto.

* * * * *